United States Patent
Takii et al.

(10) Patent No.: US 10,470,658 B2
(45) Date of Patent: Nov. 12, 2019

(54) OPTOMETRY APPARATUS AND OPTOMETRY PROGRAM

(71) Applicant: NIDEK CO., LTD., Gamagori, Aichi (JP)

(72) Inventors: Michihiro Takii, Aichi (JP); Noriji Kawai, Aichi (JP); Taeko Horino, Aichi (JP); Hisashi Ochi, Aichi (JP); Kazunori Shibata, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 121 days.

(21) Appl. No.: 15/710,202

(22) Filed: Sep. 20, 2017

(65) Prior Publication Data

US 2018/0078135 A1  Mar. 22, 2018

(30) Foreign Application Priority Data

Sep. 21, 2016 (JP) .................................. 2016-184726
Sep. 21, 2016 (JP) .................................. 2016-184727

(51) Int. Cl.
*A61B 3/08* (2006.01)
*A61B 3/10* (2006.01)
(Continued)

(52) U.S. Cl.
CPC ............... *A61B 3/18* (2013.01); *A61B 3/0025* (2013.01); *A61B 3/0091* (2013.01); *A61B 3/111* (2013.01); *A61B 3/14* (2013.01)

(58) Field of Classification Search
CPC .... A61B 3/00; A61B 3/08; A61B 3/10; A61B 3/14; A61B 3/02
(Continued)

(56) References Cited

U.S. PATENT DOCUMENTS 3,874,774 A   4/1975  Humphrey
5,483,305 A   1/1996  Kohayakawa
(Continued)

FOREIGN PATENT DOCUMENTS

JP   5-176893 A    7/1993
JP   6-217938 A    8/1994
JP   2008246143 A  10/2008

OTHER PUBLICATIONS

Communication dated Feb. 20, 2018, issued by the European Patent Office in counterpart European application No. 17192312.1.

*Primary Examiner* — Dawayne Pinkney
(74) *Attorney, Agent, or Firm* — Sughrue Mion, PLLC

(57) ABSTRACT

An optometry apparatus includes: an optical characteristic measurement device configured to measure an optical characteristic of right and left subject eyes in a both-eye opened state by projecting a visual target onto the subject eyes; an anterior ocular segment acquisition device configured to acquire anterior ocular segment images of the right and left subject eyes by the optical characteristic measurement device during the measurement of the optical characteristic of the subject eye in the both-eye opened state; and a controller configured to execute: an analysis instruction for performing analysis processing on the anterior ocular segment images acquired by the anterior ocular segment acquisition device to acquire both-eye opened state information; a determination instruction for determining whether the both-eye opened state information acquired by the analysis instruction is favorable or not, to acquire determination information; and an output instruction for outputting the determination information acquired by the determination instruction.

14 Claims, 8 Drawing Sheets

(51) Int. Cl.
*A61B 3/14* (2006.01)
*A61B 3/02* (2006.01)
*A61B 3/00* (2006.01)
*A61B 3/18* (2006.01)
*A61B 3/11* (2006.01)

(58) Field of Classification Search
USPC ........ 351/200, 201, 205, 206, 209–211, 218, 351/221–223, 245–246
See application file for complete search history.

(56) References Cited

U.S. PATENT DOCUMENTS

| | | |
|---|---|---|
| 5,777,718 A | 7/1998 | Kohayakawa |
| 2005/0174536 A1 | 8/2005 | Hanaki et al. |
| 2006/0164599 A1 | 7/2006 | Ikezawa |
| 2010/0220286 A1* | 9/2010 | Nauche .................. A61B 3/111 351/204 |
| 2016/0262611 A1* | 9/2016 | Rotenstreich ............ A61B 3/14 |

* cited by examiner

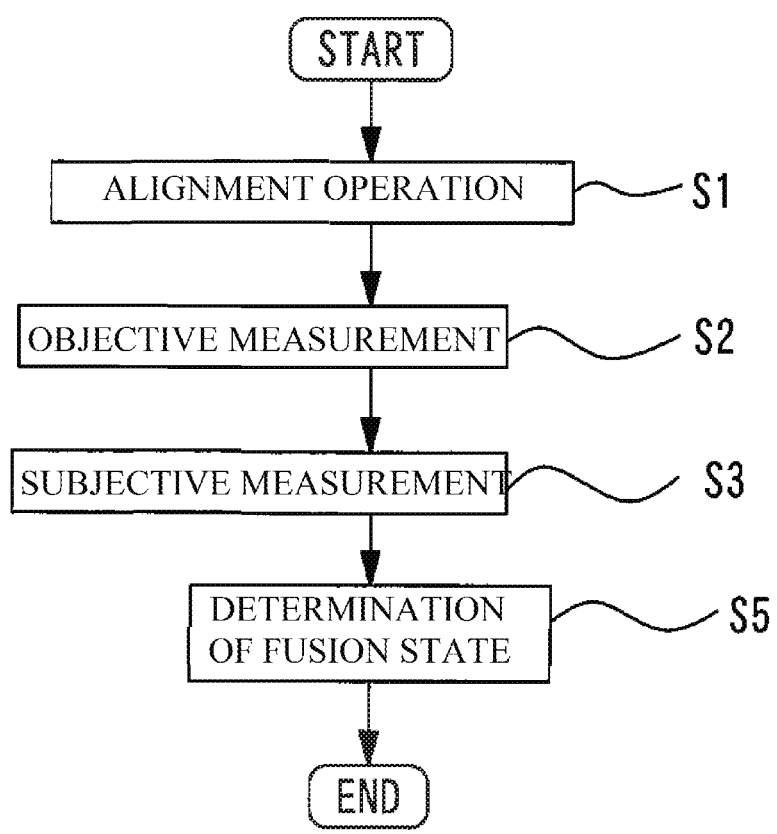

OPTOMETRY APPARATUS AND OPTOMETRY PROGRAM

BACKGROUND

The present disclosure relates to an optometry apparatus that measures an optical characteristic of a subject eye, and an optometry program.

In recent years, a subjective optometry apparatus that subjectively measures an optical characteristic and an objective optometry apparatus that objectively measures an optical characteristic have been known as optometry apparatuses. In recent years, for example, there has been known a subjective optometry apparatus which is configured such that correction optical systems capable of calibrating refractivity are individually disposed in front of an examinee's eyes, and is configured to project an examination visual target onto the fundus of the subject eye through the correction optical system (see JP-A-5-176893). An examiner receives the examinee's response and adjusts the correction optical systems until the visual target is appropriately seen by the examinee to thereby obtain a correction value, and measures a refractive power of the subject eye based on the correction value. In addition, for example, there has been known a subjective optometry apparatus which is configured such that an examination visual target image through a correction optical system is formed in front of an examinee's eye, and is configured to measure a refractive power of the subject eye without disposing the correction optical system in front of the eye (see U.S. Pat. No. 3,874,774).

The examination of a refractive power using these subjective optometry apparatuses includes a case where right and left eyes are individually examined and a case where both eyes are simultaneously examined. For example, in a case where the right and left eyes are individually examined, the eye to be examined (hereinafter, referred to as a measurement eye) is caused to observe an examination visual target. A shielding member is disposed at the eye not to be examined (hereinafter, referred to as a non-measurement eye) so that the examination visual target is not seen by the eye.

In addition, in the examination of a refractive power using these objective optometry apparatuses, the right and left eyes are individually examined. For example, in the objective optometry apparatus, an optical axis of a measurement optical system is aligned with one of the right and left eyes so as to perform measurement of one eye. At this time, the other eye is in a shielding state where the body of the apparatus is disposed in front of the eye. That is, the body of the apparatus is constituted by a shielding member, and thus the other eye is in a shielding state.

In a case where a shielding member is disposed on a non-measurement eye side when an optical characteristic of an examinee's eye is measured, the adjustment of the examinee's eye works on the shielding member, which may result in a reduction in the accuracy of measurement. For this reason, in a case where an optical characteristic of the examinee's eye is measured, it is preferable that an optical characteristic is measured through subjective measurement and an optical characteristic is measured through objective measurement under a natural state (opened state) where the examinee sees an object in daily life. As an examination method under the opened state, a method is also known in which examination is performed under a both-eye opened state by loading a plus spherical power without disposing a shielding plate on a non-measurement eye side so that fogging is applied to one eye. In addition, a method is also known in which examination is performed under a both-eye opened state by disposing a polarizing plate without disposing a shielding plate on a non-measurement eye side so that an examination visual target is not seen by one eye.

SUMMARY

Incidentally, when examination is performed in a both-eye opened state, it is not possible to confirm a fusion state of a subject eye during measurement. For this reason, in a case where examination is performed in the both-eye opened state, fusion is not successfully performed, and thus it is not possible to obtain a measurement result with a high level of accuracy.

This disclosure is contrived in view of such a problem, and an object thereof is to provide an optometry apparatus and an optometry program for easily confirming a fusion state when examination is performed in a both-eye opened state and performing measurement with a high level of accuracy.

In order to solve the above-described problem, the invention includes the following configurations.

An optometry apparatus comprising:

an optical characteristic measurement device configured to measure an optical characteristic of right and left subject eyes in a both-eye opened state by projecting a visual target onto the subject eyes;

an anterior ocular segment acquisition device configured to acquire anterior ocular segment images of the right and left subject eyes by the optical characteristic measurement device during the measurement of the optical characteristic of the subject eye in the both-eye opened state; and a controller configured to execute:

an analysis instruction for performing analysis processing on the anterior ocular segment images acquired by the anterior ocular segment acquisition device to acquire both-eye opened state information;

a determination instruction for determining whether the both-eye opened state information acquired by the analysis instruction is favorable or not, to acquire determination information; and an output instruction for outputting the determination information acquired by the determination instruction.

An optometry apparatus configured to subjectively measure an optical characteristic of a subject eye, the optometry apparatus comprising:

a light projecting optical system that includes a right eye light projecting optical system and a left eye light projecting optical system which are respectively provided as a pair on right and left sides, and projects a visual target onto the subject eyes by emitting a visual target luminous flux toward the subject eyes;

a correction optical system that includes a right eye correction optical system and a left eye correction optical system which are respectively provided as a pair on right and left sides, is disposed in an optical path of the light projecting optical system, and changes an optical characteristic of the visual target luminous flux; and a controller for controlling the light projection optical system to emit a visual target luminous flux from one 1 of the right eye light projecting optical system and the left eye light projecting optical system, project a first visual target onto one of the right and left subject eyes, emit a visual target luminous flux from the other of the right eye light projecting optical system and the left eye light projecting optical system, and project a second visual target onto the other of the right and left subject eyes, wherein the first visual target includes an examination visual target and a first background visual target, and wherein the second visual target includes a second background visual target having the same pattern as that of the first background visual target.

A non-transitory computer readable recording medium storing a computer readable program for controlling an optometry apparatus including an optical characteristic measurement device for measuring an optical characteristic of right and left subject eyes in a both-eye opened state by projecting a visual target onto the subject eyes, the computer readable program when executed by a processor of the optometry apparatus causing the optometry apparatus to execute:

an anterior ocular segment acquisition instruction for acquiring anterior ocular segment images of the right and left subject eyes by the optical characteristic measurement device during the measurement of the optical characteristic of the subject eye in the both-eye opened state;

an analysis instruction for performing analysis processing on the anterior ocular segment images acquired by the anterior ocular segment acquisition step to acquire both-eye opened state information;

a determination instruction for determining whether the both-eye opened state information acquired by the analysis step is favorable or not, to acquire determination information; and an output instruction for outputting the determination information acquired by the determination step.

BRIEF DESCRIPTION OF THE DRAWINGS

FIG. 6 is a flow chart illustrating a flow of a control operation.

DESCRIPTION OF ILLUSTRATIVE EMBODIMENTS

Figure 1:
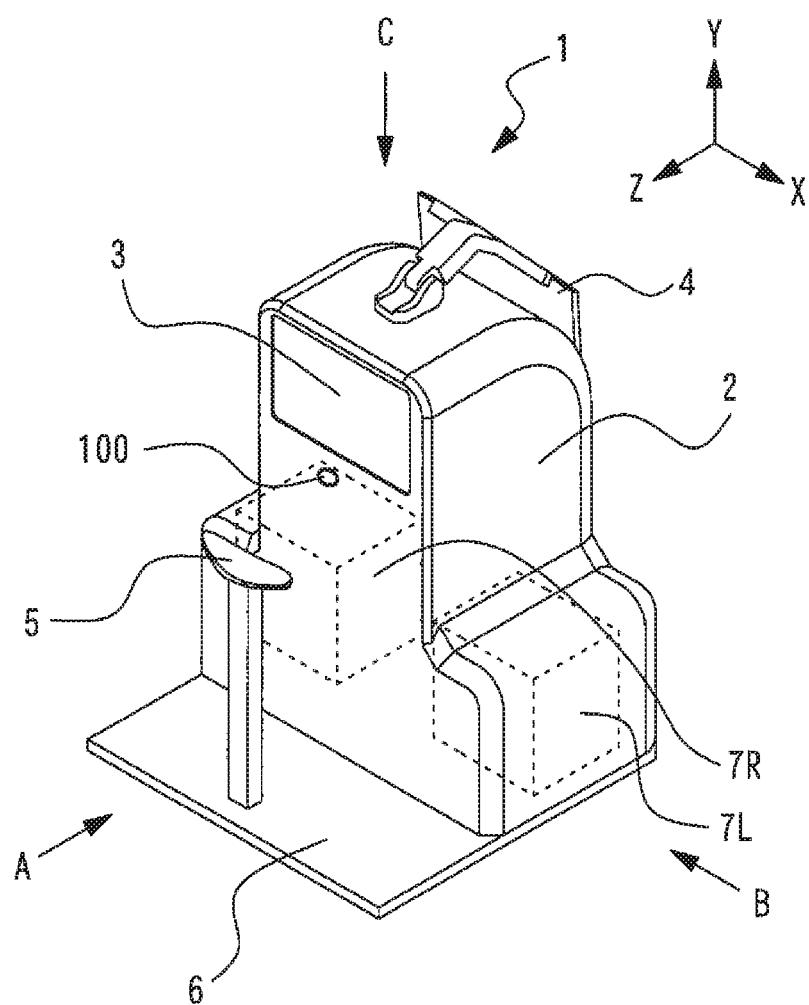
FIG. 1 is a diagram illustrating an exterior of a subjective optometry apparatus.

Hereinafter, one of typical embodiments will be described with reference to the accompanying drawings. FIGS. 1 to 9 are diagrams illustrating an optometry apparatus and an optometry program according to this embodiment. Items classified as the following sign "< >" may be used independently of or in relation to each other.

This disclosure is not limited to the apparatus described in this embodiment. For example, terminal control software (program) for performing the function of the following embodiment is supplied to a system or an apparatus through a network, any of various storage mediums, or the like. A control device (for example, a CPU or the like) of the system or the apparatus can also read out and execute a program.

In the following description, a description will be given on the assumption that a depth direction (a front-back direction of an examinee when the examinee is measured) of the optometry apparatus is a Z-direction, a horizontal direction on a plane which is perpendicular (a right-left direction of the examinee when the examinee is measured) to the depth direction is an X-direction, and a vertical direction (an up-down direction of the examinee when the examinee is measured) is a Y-direction. R and L attached to reference numerals are assumed to be signs for the right eye and the left eye, respectively.

<Outline>

For example, the optometry apparatus (for example, a subjective optometry apparatus 1) in this embodiment includes an optical characteristic measurement device (optical characteristic measurement means) (for example, a light projecting optical system 30, a correction optical system 60, a subjective measurement optical system 25, and an objective measurement optical system 10). In addition, for example, the optometry apparatus includes an anterior ocular segment acquisition device (anterior ocular segment acquisition means) (for example, a controller 70, a first index projection optical system 45, a second index projection optical system 46, and an observation optical system 50). In addition, for example, the optometry apparatus execute an analysis instruction (analysis means) by, for example, the controller 70. In addition, for example, the optometry apparatus execute a determination instruction (determination means) by, for example, the controller 70). In addition, for example, the optometry apparatus executes an output instruction (output means) by, for example, the controller 70.

In this embodiment, a configuration may also be adopted in which devices for executing the analysis instruction (analysis means), the determination instruction (determination means), and the output instruction (output means) are also served by a single device. On the other hand, for example, a configuration may also be adopted in which the analysis instruction, the determination instruction, and the output instruction may be separately executed by separate devices. Naturally, the above-described each devices may be executed by a single of or a plurality of controller.

For example, the optical characteristic measurement device may project a visual target onto the right and left subject eyes to measure an optical characteristic of the subject eye in a both-eye opened state. For example, the both-eye opened state may be a state (a state where confirmation can be performed without shielding a luminous flux of the visual target) where the right and left subject eyes are not shielded by a shielding member. For example, the anterior ocular segment acquisition device may acquire anterior ocular segment images of the respective right and left subject eyes by the optical characteristic measurement device during the measurement of an optical characteristic of the subject eye in the both-eye opened state. For example, the analysis instruction may perform analysis processing on the anterior ocular segment images acquired by the anterior ocular segment acquisition device to acquire both-eye opened state information. For example, the determination instruction may determine whether the both-eye opened state information acquired by the analysis instruction is favorable or not to acquire determination information. For example, the output instruction may output determination information acquired by the determination instruction.

For example, the optometry apparatus in this embodiment is configured to acquire anterior ocular segment images of the respective right and left subject eyes during the measurement of an optical characteristic of the subject eye in the both-eye opened state, and to acquire both-eye opened state information by performing analysis processing on the acquired anterior ocular segment images. In addition, the optometry apparatus is configured to determine whether being favorable or not based on the acquired both-eye opened state information and to output a determination result. Thereby, it is possible to easily confirm whether a fusion state of the subject eye during measurement is favorable or not, and to acquire a measurement result under a state where the fusion state is favorable. Thereby, it is possible to obtain a highly accurate measurement result.

For example, a configuration may also be adopted in which the both-eye opened state information is acquired during the measurement of an optical characteristic by the optical characteristic measurement device. For example, the optometry apparatus may execute transmission instruction for transmitting a start trigger signal for starting the acquisition of anterior ocular segment images of the respective right and left subject eyes by the anterior ocular segment acquisition device, and reception instruction for receiving the start trigger signal. For example, when the start trigger signal is transmitted by the transmission instruction and is received by the reception instruction, the anterior ocular segment acquisition device acquires the anterior ocular segment images of the respective right and left subject eyes during the measurement of an optical characteristic of the subject eye in the both-eye opened state. The analysis instruction performs analysis processing on the acquired anterior ocular segment images to acquire the both-eye opened state information. Thereby, it is possible to acquire the both-eye opened state information during the measurement of an optical characteristic by the optical characteristic measurement device. For example, the start of acquisition of the anterior ocular segment images by the anterior ocular segment acquisition device may be manually performed, or may be automatically performed.

For example, in a case of a configuration in which the start of acquisition of the anterior ocular segment images is manually performed, a start switch is provided for transmitting the start trigger signal for starting the acquisition of the anterior ocular segment images to the optometry apparatus. For example, the start switch is selected by an examiner, so that the start trigger signal is transmitted. For example, when the start trigger signal is received by the reception instruction, the anterior ocular segment acquisition device may start the acquisition of the anterior ocular segment images.

For example, as a configuration in which the both-eye opened state information is acquired during the measurement of an optical characteristic by the optical characteristic measurement device, the both-eye opened state information may be acquired at least once during the measurement of an optical characteristic by the optical characteristic measurement device. That is, for example, as a configuration in which both-eye opened state information is acquired during the measurement of an optical characteristic by the optical characteristic measurement device, the both-eye opened state information may be acquired once as a minimum number of times of acquisition, and the both-eye opened state information may be acquired at all times (in real time) as a maximum number of times of acquisition.

For example, in a case where both-eye opened state information is desired to be acquired once, the examiner may select the start switch once during the measurement of an optical characteristic by the optical characteristic measurement device to acquire an anterior ocular segment image and to acquire the both-eye opened state information.

In addition, for example, in a case where both-eye opened state information is desired to be acquired a plurality of times, the examiner may select the start switch a plurality of times during the measurement of an optical characteristic by the optical characteristic measurement device to acquire the both-eye opened state information a plurality of times. In addition, for example, in a case where the both-eye opened state information is desired to be acquired a plurality of times, the examiner may select the start switch once during the measurement of an optical characteristic by the optical characteristic measurement device to acquire the both-eye opened state information a plurality of times.

For example, in a case where the start trigger signal is output once to acquire the both-eye opened state information a plurality of times, the examiner may select the start switch once during the measurement of an optical characteristic by the optical characteristic measurement device to acquire the both-eye opened state information a preset number of times. In addition, for example, in a case where the start trigger signal is output once to acquire the both-eye opened state information a plurality of times, the examiner may select the start switch once during the measurement of an optical characteristic by the optical characteristic measurement device to acquire the both-eye opened state information at a preset timing. In addition, for example, in a case where the start trigger signal is output once to acquire the both-eye opened state information a plurality of times, the examiner may select the start switch once during the measurement of an optical characteristic by the optical characteristic measurement device to acquire the both-eye opened state information at all times and to acquire the both-eye opened state information in real time.

For example, in a case of a configuration in which the start of acquisition of the anterior ocular segment image is automatically performed, the controller (for example, the controller 70) may control the transmitter so as to transmit the start trigger signal at a preset timing after the measurement of an optical characteristic is started by the optical characteristic measurement device. For example, when the start trigger signal is received by the receiver, the anterior ocular segment acquisition device may start the acquisition of the anterior ocular segment image. In this embodiment, the control of the transmitter is performed by the controller, but is not limited thereto. For example, the start of acquisition of the anterior ocular segment image may be performed by separately providing different controller.

For example, the preset timing may be at least one of a timing when the measurement of an optical characteristic by the optical characteristic measurement device is started (for example, a state where the projection of a visual target is started, a state where an examination program is started, a state where the operation of an operation portion of an examination apparatus is started, a state where the driving of a correction optical system is started, and the like), a timing when a preset time elapses (for example, a timing when a predetermined time elapses from the start of measurement of an optical characteristic by the optical characteristic measurement device, or the like), a timing when the visual target is switched, a timing when the examinee makes a response in a subjective examination (a timing when the examiner performs an operation based on the examinee's response), and the like. Naturally, the start trigger signal may be output at a timing other than the above-described timings.

For example, as a configuration in which the both-eye opened state information is acquired during the measurement of an optical characteristic by the optical characteristic measurement device, the both-eye opened state information may be acquired at least once during the measurement of an optical characteristic by the optical characteristic measurement device. That is, for example, as a configuration in which the both-eye opened state information is acquired during the measurement of an optical characteristic by the optical characteristic measurement device, the both-eye opened state information may be acquired once as a minimum number of times of acquisition, or the both-eye opened state information may be acquired at all times (in real time) as a maximum number of times of acquisition.

For example, in a case where the both-eye opened state information is desired to be acquired once, the start trigger is output at a preset timing during the measurement of an optical characteristic by the optical characteristic measurement device and the anterior ocular segment image may be output, so that the both-eye opened state information may be acquired.

In addition, for example, in a case where the both-eye opened state information is desired to be acquired a plurality of times, the start trigger may be output at a preset timing during the measurement of an optical characteristic by the optical characteristic measurement device so that the both-eye opened state information is acquired a plurality of times. In this case, for example, the start trigger signal may be output a plurality of times during the measurement of an optical characteristic by the optical characteristic measurement device so that the both-eye opened state information is acquired a plurality of times. In this case, for example, the start trigger signal may be output once during the measurement of an optical characteristic by the optical characteristic measurement device so that the both-eye opened state information is acquired a plurality of times.

For example, in a case where the start trigger signal is output once so that the both-eye opened state information is acquired a plurality of times, the start trigger may be output once during the measurement of an optical characteristic by the optical characteristic measurement device so that the both-eye opened state information is acquired a preset number of times. In addition, for example, in a case where the start trigger signal is output once so that the both-eye opened state information is acquired a plurality of times, the start trigger may be output once during the measurement of an optical characteristic by the optical characteristic measurement device so that the both-eye opened state information is acquired a plurality of times at a preset timing. In addition, for example, in a case where the start trigger signal is output once so that the both-eye opened state information is acquired a plurality of times, measurement may be performed at all times so that the time both-eye opened state information is acquired in real time.

<Optical Characteristic Measurement Device>

For example, in a case where an optical characteristic of the subject eye is measured, a visual target may be projected onto the subject eye so that measurement is performed in a state where the examinee is caused to observe the visual target. For example, a configuration may also be adopted in which the visual target is projected onto each of the right and left subject eyes in a case where an optical characteristic is measured in a both-eye opened state.

For example, the configuration in which an optical characteristic of the subject eye is measured in the both-eye opened state may be a configuration in which the visual target is presented to each of the right and left subject eyes so as to measure an optical characteristic in both eyes. In this case, for example, the configuration in which an optical characteristic of the subject eye is measured in the both-eye opened state may be a configuration in which the measurement is performed in a state where the visual target is presented to each of the right and left subject eyes.

In addition, for example, the configuration in which an optical characteristic of the subject eye is measured in the both-eye opened state may be a configuration in which the measurement is performed in one eye by presenting the visual target to each of the right and left subject eyes. For example, in a case of a configuration in which the measurement is performed in one eye, the measurement is performed by providing a configuration in which the visual target for measuring an optical characteristic is projected onto one subject eye, the visual target is projected onto the other subject eye, and a luminous flux of the visual target projected onto the other subject eye is not completely shielded.

For example, the configuration in which an optical characteristic of one eye is measured in a both-eye opened state may be a configuration in which a visual target (for example, a first visual target 200 and a third visual target 230) which has an examination visual target (for example, an examination visual target 201 and an examination visual target 231) for measuring an optical characteristic and a background visual target (for example, a first background visual target 202 and a third background visual target 232) is projected onto one subject eye, and a visual target (for example, a second visual target 210 and a fourth visual target 240) which has a background visual target (for example, a second background visual target 212 and a fourth background visual target 242) is projected onto the other subject eye. In addition, for example, the configuration in which an optical characteristic of one eye is measured in a both-eye opened state may be a configuration in which an examination visual target for measuring an optical characteristic is projected onto one subject eye, a visual target is projected onto the other subject eye, and fogging is applied by loading a plus spherical power without disposing a shielding plate at the other subject eye. In addition, for example, the configuration in which an optical characteristic of one eye is measured in a both-eye opened state may be a configuration in which an examination visual target for measuring an optical characteristic is projected onto one subject eye, a visual target is projected onto the other subject eye, and a polarizing plate is disposed at the other subject eye instead of a shielding plate.

<Subjective Measurement Device>

For example, the optical characteristic measurement device may include subjective measurement device. In this case, for example, the optical characteristic measurement device may include subjective measurement device including a correction optical system (for example, the correction optical system 60 and the subjective measurement optical system 25) which is disposed in an optical path of a light projecting optical system (for example, the light projecting optical system 30) projecting a visual target luminous flux toward the subject eye and changes an optical characteristic of the visual target luminous flux, and subjectively measuring an optical characteristic of the subject eye. For example, the light projecting optical system may not be integrally provided in the optometry apparatus, and a configuration may also be adopted in which an apparatus including a light projecting optical system is separately provided. That is, the optometry apparatus may be configured to include at least a correction optical system.

For example, the subjective measurement device subjectively measures an optical characteristic of a subject eye. Examples of the optical characteristic of the subject eye which is subjectively measured include an eye refractive power (for example, a spherical power, an astigmatic power, an astigmatic axis angle, and the like), a contrast sensitivity, binocular vision function (for example, the amount of oblique position, a stereoscopic function, and the like), and the like.

<Light Projecting Optical System>

For example, the light projecting optical system includes a light source that emits a visual target luminous flux. In addition, for example, the light projecting optical system may include at least one or more optical members that guide the visual target luminous flux projected from the light source projecting the visual target luminous flux toward a subject eye.

For example, a configuration may also be adopted in which a display (for example, a display 31) is used as the light source that projects the visual target luminous flux. For example, a liquid crystal display (LCD), an organic electroluminescence (EL), or the like is used as the display. For example, an examination visual target such as a Landolt ring visual target is displayed on the display.

For example, a light source and a digital micromirror device (DMD) may be used as the light source that projects the visual target luminous flux. In general, the DMD has high reflectivity and luminance. For this reason, it is possible to maintain the amount of light of the visual target luminous flux as compared to a case where a liquid crystal display using polarization is used.

For example, the light source projecting the visual target luminous flux may be configured to include a visual target presentation visible light source and a visual target plate. In this case, for example, the visual target plate is a rotatable disc plate, and includes a plurality of visual targets. The plurality of visual targets include, for example, a visual target for examination of visual acuity which is used during subjective measurement, and the like. For example, regarding the visual target for examination of visual acuity, a visual target (visual acuity value 0.1, 0.3, . . . , 1.5) is provided for each visual acuity value. For example, the visual target plate is rotated by a motor or the like, and the visual targets are disposed in a switching manner on an optical path through which the visual target luminous flux is guided to the subject eye. Naturally, a light source other than the light source having the above-described configuration may be used as the light source projecting the visual target luminous flux.

For example, in this embodiment, the light projecting optical system may include a right eye light projecting optical system and a left eye light projecting optical system which are respectively provided as a pair on the right and left sides. For example, the right eye light projecting optical system and the left eye light projecting optical system may be configured such that members constituting the right eye light projecting optical system and members constituting the left eye light projecting optical system are constituted by the same member. In addition, for example, the right eye light projecting optical system and the left eye light projecting optical system may be configured such that at least some of members constituting the right eye light projecting optical system and members constituting the left eye light projecting optical system are constituted by different members. For example, the right eye light projecting optical system and the left eye light projecting optical system may be configured such that at least some of members constituting the right eye light projecting optical system and members constituting the left eye light projecting optical system are also served. In addition, for example, the right eye light projecting optical system and the left eye light projecting optical system may be configured such that members constituting the right eye light projecting optical system and members constituting the left eye light projecting optical system are separately provided.

<Correction Optical System>

For example, the correction optical system may be configured to change an optical characteristic (for example, at least any one of a spherical power, a cylindrical power, a cylindrical axis, a polarization characteristic, the amount of aberration, and the like) of a visual target luminous flux. For example, as a configuration in which the optical characteristic of the visual target luminous flux is changed, a configuration in which an optical element is controlled may be adopted. For example, as the optical element, a configuration may also be adopted in which at least any one of a spherical lens, a cylindrical lens, a cross cylinder lens, a rotary prism, a wavefront modulation element, and the like is used. Naturally, for example, as the optical element, an optical element different from the optical element having the above-described configuration may be used.

For example, the correction optical system may be configured such that a spherical power of a subject eye is corrected by a presentation position (presenting distance) of a visual target with respect to an examinee's eye is optically changed. In this case, for example, as a configuration in which the presentation position (presenting distance) of the visual target is optically changed, a configuration may also be adopted in which a light source (for example, display) is moved in an optical axis direction. In addition, in this case, for example, a configuration may also be adopted in which the optical element (for example, a spherical lens) which is disposed in the optical path is moved in the optical axis direction. Naturally, the correction optical system may have a configuration constituted by a configuration in which the optical element is controlled and a configuration in which the optical element disposed in the optical path is moved in the optical axis direction.

For example, the correction optical system may be an optometry unit (phoropter) in which optical elements disposed in front of a subject eye are disposed in a switching manner. For example, the optometry unit may be configured to include a lens disc having a plurality of optical elements disposed on the same circumference thereof and driver for rotating the lens disc, and to electrically switch the optical elements by the driving of the driver (for example, a motor).

For example, the correction optical system may be configured to change an optical characteristic of a visual target luminous flux by disposing an optical element between an optical member for guiding the visual target luminous flux toward the subject eye from the light projecting optical system and the light source of the light projecting optical system and by controlling the optical element. That is, the calibrator may have a configuration of a phantom lens refractometer (phantom correction optical system). In this case, for example, the visual target luminous flux corrected by the correction optical system is guided to the subject eye through the optical member.

For example, in this embodiment, the correction optical system includes a right eye correction optical system and a left eye correction optical system which are respectively provided as a pair on the right and left sides. For example, the right eye correction optical system and the left eye correction optical system may be configured such that members constituting the right eye correction optical system and members constituting the left eye correction optical system are constituted by the same member. In addition, for example, the right eye correction optical system and the left eye correction optical system may be configured such that at least some of members constituting the right eye correction optical system and members constituting the left eye correction optical system are constituted by different members. For example, the right eye correction optical system and the left eye correction optical system may be configured such that at least some of members constituting the right eye correction optical system and members constituting the left eye correction optical system are used in common. In addition, for example, the right eye correction optical system and the left eye correction optical system may be configured such that members constituting the right eye correction optical system and members constituting the left eye correction optical system are separately provided.

<Objective Measurement Device>

For example, the optical characteristic measurement device may include an objective measurement device. For example, the objective measurement device objectively measures an optical characteristic of the subject eye. In a case where the measurement is performed by the objective measurement device, a visual target may be projected onto the subject eye so that the measurement is performed in a state where the examinee is caused to observe the visual target. That is, in a case where the measurement is performed by the objective measurement device, a fixation target may be projected in order to lead a gaze direction of the subject eye so that the measurement is performed in a state where the examinee is caused to observe the fixation target.

Examples of the optical characteristic of the subject eye which is objectively measured include an eye refractive power (for example, a spherical power, an astigmatic power, an astigmatic axis angle, and the like), a polarization characteristic, thickness information of a crystalline lens, and the like. In this embodiment, an example of the objective measurement device measuring an eye refractive power of the subject eye will be described. For example, the objective measurement device includes a measurement optical system (for example, an objective measurement optical system 10) that emits measurement light to the fundus of the subject eye and receives the reflected light thereof. For example, the optical characteristic of the subject eye which is objectively measured may be at least any one of an image capture result (captured image) which is imaged by the objective measurement device and a parameter which is acquired by analyzing and processing the image capture result. That is, the optical characteristic of the subject eye which is objectively measured may be an optical characteristic based on the image capture result imaged by the objective measurement device.

For example, the objective measurement device may include a right subject eye measurement optical system and a left subject eye measurement optical system which are provided on the right and left sides, respectively, as a pair. In this case, for example, the right subject eye measurement optical system and the left subject eye measurement optical system may be configured to execute measurement on the right side and measurement on the left side at substantially the same time. In addition, in this case, for example, measurement by the right subject eye measurement optical system and measurement by the left subject eye measurement optical system may be performed at different timings. For example, the different timings may be timings when the measurement of either the right subject eye measurement optical system or the left subject eye measurement optical system is completed. In addition, for example, the different timings may be during the measurement of either the right subject eye measurement optical system or the left subject eye measurement optical system.

In addition, for example, the objective measurement device may be configured such that the measurement of the right subject eye and the measurement of the left subject eye are performed by one measurement optical system. In this case, for example, a configuration may also be adopted in which in a case where measurement light is emitted to the fundus of one subject eye to measure the subject eye and the measurement of one eye is completed, adjustment is performed so that measurement light can be emitted to the fundus of the other subject eye, thereby measuring the other subject eye.

<Measurement Optical System>

For example, the measurement optical system includes a light projecting optical system that projects measurement light from a light source toward an examinee's fundus, and an image capture optical system that images reflected light, acquired by the reflection of the measurement light from the fundus, by the image capture element. For example, the measurement optical system may be an optical system that measures an eye refractive power of a subject eye. In this case, examples of a configuration of the measurement optical system include a configuration in which a spot-shaped measurement index is projected onto the subject eye's fundus through a pupil central portion of the subject eye, fundus reflected light reflected from the fundus is taken out in the form of a ring through a pupil peripheral portion, and a ring-shaped fundus reflected image is captured by the image capture element. In addition, in this case, examples of a configuration of the measurement optical system include a configuration in which a ring-shaped measurement index is projected onto the fundus from the pupil peripheral portion, the fundus reflected light is taken out from the pupil central portion, and the ring-shaped fundus reflected image is captured by the image capture element. In addition, in this case, for example, the measurement optical system may be configured to include a Shack Hartman sensor. In addition, in this case, for example, the measurement optical system may be configured to have a phase difference scheme in which a slit is projected onto the subject eye.

<Anterior Ocular Segment Acquisition Device>

For example, the anterior ocular segment acquisition device may be configured to image an anterior ocular segment by an anterior ocular segment imaging optical system included in the optometry apparatus to acquire an anterior ocular segment. In addition, for example, the anterior ocular segment acquisition device may be configured to acquire an anterior ocular segment by receiving an anterior ocular segment image captured by an anterior ocular segment imaging optical system of an apparatus different from the optometry apparatus.

For example, a configuration may also be adopted in which anterior ocular segment images of the respective right and left subject eyes includes the irises (for example, pupil portions and iris portions) in the right and left subject eyes. In addition, for example, a configuration may also be adopted in which the anterior ocular segment images of the respective right and left subject eyes include pupil portions of the right and left subject eyes. In addition, for example, a configuration may also be adopted in which the anterior ocular segment images of the respective right and left subject eyes include the entirety of the right and left subject eyes.

For example, the anterior ocular segment imaging optical system may be configured to include an illumination optical system (for example, the second index projection optical system 46) for illuminating the anterior ocular segment, and an imaging optical system (for example, the observation optical system 50) which images the anterior ocular segment illuminated by the illumination optical system. For example, the illumination optical system may be configured to also serve as a light source of another optical system. In addition, for example, the illumination optical system may be configured such that s dedicated light source for illuminating the anterior ocular segment is separately provided. For example, the imaging optical system may be configured to also serve as an image capture element of another optical system. In addition, for example, the imaging optical system may be configured such that a dedicated image capture element (for example, a two-dimensional image capture element 52) for imaging the anterior ocular segment is separately provided.

For example, as a configuration in which anterior ocular segment images of the respective right and left subject eyes are acquired, a configuration may also be adopted in which the anterior ocular segment acquisition device acquires the anterior ocular segment images so that anterior ocular segments of the right and left subject eyes are included in one anterior ocular segment image. In this case, for example, the imaging of the anterior ocular segment may be performed using an anterior ocular segment imaging optical system capable of performing imaging in a range in which the right and left anterior ocular segments are included in an imaging range.

In addition, for example, as a configuration in which anterior ocular segment images of the respective right and left subject eyes are acquired, a configuration may also be adopted in which the anterior ocular segment images are acquired so that anterior ocular segments of the right and left subject eyes are included in a plurality of anterior ocular segment images that are simultaneously acquired. For example, a configuration may also be adopted in which one anterior ocular segment image is acquired in each of the right and left subject eyes. In this case, for example, a configuration may also be adopted in which anterior ocular segment imaging optical systems provided to respectively image the right and left subject eyes are provided, and the right and left anterior ocular segments are respectively imaged by right and left anterior ocular segment imaging optical systems. In addition, in this case, for example, a configuration may also be adopted in which one anterior ocular segment imaging optical system captures right and left anterior ocular segment images by moving to positions at which the right and left subject eyes can be respectively imaged.

For example, as a configuration in which anterior ocular segment images of the respective right and left subject eyes are acquired during the measurement of an optical characteristic of the subject eye in a both-eye opened state by the optical characteristic measurement device, a configuration may also be adopted in which the measurement is performed by projecting a visual target onto the right and left subject eyes.

<Analysis Instruction>

For example, the analysis instruction executed by the controller may perform analysis processing on an anterior ocular segment image to acquire both-eye opened state information. For example, the analysis processing may be processing for detecting each region (for example, an iris, an iris portion, a pupil portion, a scleral portion (white portion), and the like). In addition, for example, the analysis processing may be processing for projecting an index onto the cornea of the subject eye and detecting an index image formed on the cornea of the subject eye. Naturally, the analysis processing may be processing for detecting each region or a region different from the index image.

For example, the processing for detecting each region or an index image through analysis processing may be processing for performing edge detection. In this case, for example, a configuration may also be adopted in which the edge detection includes detecting a rise and a fall in luminance. Naturally, the analysis processing may be processing for detecting each region or an index image through image processing.

For example, the both-eye opened state information may be information indicating a both-eye fusion state with respect to a visual target. For example, a configuration may also be adopted in which the both-eye opened state information is acquired from detection results of the right and left subject eyes. In this case, for example, the detection results of the respective right and left subject eyes may be acquired so that both-eye opened state information is acquired based on the acquired detection results. In addition, for example, a configuration may also be adopted in which the both-eye opened state information is acquired from one subject eye of the right and left subject eyes. In addition, in this case, for example, the both-eye opened state information is acquired based on a detection result of at least one subject eye of the right and left subject eyes.

For example, the analysis instruction may detect each region or an index image through analysis processing so that both-eye opened state information is acquired based on a detection result. For example, the both-eye opened state information may be at least one of pupil information, cornea apex information, and the like. The both-eye opened state information is not limited to the above-described configuration. For example, the both-eye opened state information may be information for acquiring a gaze position (visual axis position) of the subject eye.

For example, in a case where pupil information is acquired as the both-eye opened state information, the analysis instruction performs analysis processing on an anterior ocular segment image to detect pupil positions of the right and left subject eyes and to acquire the both-eye opened state information based on the detected pupil positions. For example, the optometry apparatus in this embodiment is configured to detect the pupil positions of the right and left subject eyes and to acquire the both-eye opened state information based on the detected pupil positions. Thereby, it is possible to easily acquire the both-eye opened state information with a simple configuration. For example, the pupil information may be at least any one of distance-between-pupils information, pupil position information, pupil positional shift information, and the like. For example, the pupil position may be a position of any one portion of the pupil region. In addition, for example, the pupil position may be the center position of the pupil. Naturally, the pupil position information may be information different from the above-described pieces of information. For example, the pupil position information may be information calculated based on the pupil position. That is, the pupil position information may be information for specifying the pupil position.

For example, in a case where cornea apex information is acquired as the both-eye opened state information, the analysis instruction performs analysis processing on an anterior ocular segment image to detect an index image projected onto the corneas of the right and left subject eyes and to acquire the both-eye opened state information based on the position of the detected index image. For example, the cornea apex information may be at least any one of cornea apex position information, distance-between-corneas information, cornea apex shift information, and the like. Naturally, the cornea apex information may be information different from the above-described pieces of information. For example, the cornea apex information may be information calculated based on the position of the index image. That is, the cornea apex information may be information for specifying the cornea apex position.

For example, the both-eye opened state information may be information calculated from the pupil position information and the cornea apex position information. For example, the information calculated from the pupil position information and the cornea apex position information may be information on a shift between the pupil position and the cornea apex position. For example, the pupil position may be position of any one portion of the pupil region. In addition, for example, the pupil position may be the center position of the pupil. Naturally, the information calculated from the pupil position information and the cornea apex position information may be information different from the above-described pieces of information. For example, the information calculated from the pupil position information and the cornea apex position information may be information calculated from the pupil position and the position of the index image. That is, the information calculated from the pupil position information and the cornea apex position information may be information for specifying the pupil position and the cornea apex position. A configuration may also be adopted in which the cornea apex information is acquired by detecting the cornea position from the anterior ocular segment image without using an index image.

For example, the pupil positional shift information can be acquired by calculating the amount of movement of the pupil position information acquired during measurement of reference pupil position information. For example, the reference pupil position information may be set the at a pupil position (average pupil position of a person) which is based on an average distance-between-pupils of a person. In addition, for example, a configuration may also be adopted in which the pupil position in a state where a both-eye opened state of the examinee to be measured is favorable is detected to acquire pupil position information in advance, and the pupil position information acquired in advance is set as reference position information.

For example, as a configuration in which the pupil position is acquired in advance, the anterior ocular segment acquisition device acquires a first anterior ocular segment image in advance before determining whether the both-eye opened state is favorable or not during the measurement of an optical characteristic of the subject eye. For example, the analysis instruction detects the pupil position from the acquired first anterior ocular segment image to acquire first pupil position information. In addition, when it is determined whether the both-eye opened state is favorable or not during the measurement of an optical characteristic of the subject eye, the anterior ocular segment acquisition device acquires a second anterior ocular segment image. The analysis instruction detects the pupil position from the acquired second anterior ocular segment image to acquire second pupil position information. The analysis instruction can acquire pupil positional shift information by calculating the amount of movement based on the first pupil position information and the second pupil position information. For example, a configuration may also be adopted in which the first anterior ocular segment image is acquired before the second anterior ocular segment image is acquired after the measurement of an optical characteristic of the subject eye is started. In addition, for example, a configuration may also be adopted in which the first anterior ocular segment image is acquired by reproducing and imaging the both-eye fusion state in advance before the measurement is started. For example, in a case where the first anterior ocular segment image is acquired, the first anterior ocular segment image may be acquired by setting one subject eye to be in an opened state (a state where a visual target is observed) and setting the other subject eye to be in a shielding state. In addition, for example, in a case where the second anterior ocular segment image is acquired, the second anterior ocular segment image may be acquired by setting one subject eye to be in an opened state (a state where a visual target is observed) and setting the other subject eye to be in a shielding state.

For example, the analysis instruction may acquire both-eye opened state information based on at least one or more anterior ocular segment images of the right and left subject eyes. For example, the both-eye opened state information may be acquired by acquiring an anterior ocular segment image obtained by averaging a plurality of anterior ocular segment images of the right and left subject eyes and performing analysis processing on the acquired anterior ocular segment image. In addition, for example, the both-eye opened state information may be acquired by acquiring both-eye opened state information from each of the plurality of anterior ocular segment images of the right and left subject eyes and averaging the acquired plurality of pieces of both-eye opened state information.

<Determination Instruction>

For example, the determination instruction executed by the controller may acquire determination information by determining whether both-eye opened state information acquired by the analysis instruction is favorable or not. For example, the determination instruction may determine whether or not the both-eye opened state information is favorable or not by comparing the acquired both-eye opened state information and reference data with each other in a case where it is determined whether the both-eye opened state information is favorable or not. In this case, for example, the determination instruction may determine whether the both-eye opened state information is favorable or not, based on whether or not the acquired both-eye opened state information exceeds the reference data. In addition, in this case, the determination instruction may determine whether the both-eye opened state information is favorable or not, based on whether or not the acquired both-eye opened state information is the same as the reference data. In this example, the wording "the same" may include being substantially the same.

For example, the reference data may be stored in a memory (for example, a memory 72). In this case, for example, the determination instruction may call the reference data from the memory when performing determination processing, and may set the reference data.

For example, the reference data may be a preset threshold value. For example, regarding the reference data, reference data for determining that the both-eye opened state is favorable through simulation, experiment, or the like may be set in advance. For example, a configuration may also be adopted in which the reference data can be arbitrarily set by the examiner.

For example, the reference data may be reference data for the pupil information. In this case, for example, regarding the reference data, reference data for at least any one of the distance-between-pupils information, the pupil position information, the pupil positional shift information, and the like may be set. In addition, for example, the reference data may be reference data for the cornea apex information. In this case, for example, regarding the reference data, reference data for at least any one of the cornea apex position information, the distance-between-corneas information, the cornea apex shift information, and the like may be set.

For example, the determination information may be a determination result (result indicating whether or not the both-eye opened state is favorable or not). In addition, for example, the determination information may be guide information (for example, warning information indicating that the both-eye opened state is not set, information for promoting the confirmation of the both-eye opened state, information for promoting the adjustment of the both-eye opened state, or the like) based on the determination result. Naturally, the determination information is not limited to the above-described configuration, and may be information for identifying whether the both-eye opened state is favorable or not.

For example, the determination instruction may determine whether or not the both-eye fusion state is stabilized. In this case, for example, anterior ocular segment image acquisition instruction executed by the controller acquires a plurality of anterior ocular segment images during the measurement of an optical characteristic. For example, the analysis instruction may perform analysis processing on the acquired anterior ocular segment images to acquire a plurality of pieces of both-eye opened state information. For example, the determination instruction sequentially performs determination processing on the acquired plurality of pieces of both-eye opened state information, and performs determination based on whether or not the pieces of both-eye opened state information exceed the reference data. For example, the determination instruction may determine that the pieces of both-eye opened state information are not stabilized in a case where it is determined that a predetermined number of pieces of both-eye opened state information, among the plurality of pieces of both-eye opened state information, are not favorable. Naturally, the determination of stability is not limited to the above-described configuration. For example, the determination instruction may determine that the pieces of both-eye opened state information are not stabilized in a case where the pieces of both-eye opened state information determined not to be favorable consecutively continue. Stability information acquired by the determination instruction may be output by the output instruction.

<Output Instruction>

For example, the output instruction executed by the controller may output the determination information acquired by the determination instruction. For example, the output instruction may be configured to display the determination information on a display. In addition, for example, the output instruction may be configured to print the determination information. For example, the output instruction may be configured to transmit the determination information toward another apparatus (another controller). In this case, for example, another apparatus may receive the determination information and may perform a variety of control based on received adjustment information.

<Distance Changing Instruction>

For example, the optometry apparatus may execute a distance changing instruction (distance changing means) by, for example, the controller 70 to control, for example, the light projecting optical system 30. For example, the distance changing instruction may change a presenting distance of a visual target to the right and left subject eyes by the optical characteristic measurement device. For example, in a case where the presenting distance is changed, the anterior ocular segment acquisition device may acquire an anterior ocular segment image during the measurement of an optical characteristic of the subject eye in a both-eye opened state in the changed presenting distance in a case where the presenting distance is changed by the distance changing instruction. For example, the analysis instruction may perform analysis processing on the anterior ocular segment image in the changed presenting distance, and may acquire both-eye opened state information in the changed presenting distance.

For example, the optometry apparatus in this embodiment is configured to change a presenting distance of a visual target to the right and left subject eyes, and to acquire an anterior ocular segment image during the measurement of an optical characteristic of the subject eye in the both-eye opened state in the changed presenting distance in a case where the presenting distance is changed. Thereby, it is possible to confirm whether or not the examinee can perform fusion based on the changed presenting distance. That is, it is possible to prevent measurement from being performed based on the presenting distance by which the examinee cannot perform fusion, and to obtain a highly accurate measurement result.

For example, presenting distance changing instruction may be configured to change the position of a light source irradiating a visual target. In this case, for example, a configuration may also be adopted in which the light source irradiating the visual target is moved in the optical axis direction so as to change a presenting distance. In addition, for example, the presenting distance changing instruction may be configured to change the presenting distance by driving an optical member disposed in the optical path in which the visual target is projected onto the subject eye. In this case, for example, the configuration in which the optical member is driven may be a configuration in which the optical member is moved in the optical axis direction. In addition, in this case, for example, a configuration in which the optical member is driven may be a configuration in which the optical member is inserted into or removed from the optical axis. In addition, in this case, for example, the configuration in which the optical member is driven may be a configuration in which the optical member is moved (for example, at least any one of linear movement, rotational movement, and the like). In addition, in this case, for example, the configuration in which the optical member is driven may be a configuration in which the optical member is changed (an optical member disposed in the optical axis, among a plurality of optical members, is selected). For example, the optical member may be at least one of a mirror, a prism, a lens, and the like. Naturally, the optical member is not limited to the above-described configuration.

For example, as the change of the presenting distance, a configuration may be adopted in which a change to at least one or more presenting distances is made. For example, the configuration in which a change to at least one or more presenting distances is made may be a configuration in which a change to one presenting distance is made. For example, the configuration in which a change to one presenting distance is made may be a configuration in which setting to a presenting distance which is arbitrarily set by the examiner is performed. For example, the configuration in which a change to one presenting distance is made may be a configuration in which setting to a preset presenting distance is performed.

For example, as the configuration in which setting to a presenting distance which is arbitrarily set by the examiner is performed, the operation portion may be operated by the examiner so that any presenting distance is set. For example, the presenting distance changing instruction may change the presenting distance of a visual target to the presenting distance which is set by the examiner.

For example, the configuration in which a change to at least one or more presenting distances is made may be a configuration in which the presenting distance of the visual target is changed to a plurality of presenting distances. In this case, for example, the distance changing instruction may change the presenting distance of the visual target to a plurality of presenting distances. For example, the anterior ocular segment acquisition device may acquire an anterior ocular segment image during the measurement of an optical characteristic of the subject eye in a both-eye opened state for each position where the presenting distance is changed when a change to a plurality of presenting distances is made by the distance changing instruction. For example, the analysis instruction may perform analysis processing on the anterior ocular segment image, and may acquire both-eye opened state information for each position where the presenting distance is changed. For example, the optometry apparatus in this embodiment makes a change to a plurality of presenting distances, and acquires an anterior ocular segment image during the measurement of an optical characteristic of the subject eye in a both-eye opened state for each position where the presenting distance is changed. Thereby, it is possible to confirm a presenting distance by which the examinee cannot perform fusion, and to perform measurement within a range of the presenting distance to a position where the examinee cannot perform fusion. Thereby, it is possible to obtain a highly accurate measurement result.

For example, the configuration in which a presenting distance of a visual target is changed to a plurality of presenting distances may be a configuration in which a change can be made from a presenting distance at the early stage to a plurality of presenting distances. For example, as the presenting distance at the early stage, a predetermined presenting distance (for example, a presenting distance for far-sight examination (for example, 5 m or the like)) may be set. In addition, for example, as the presenting distance at the early stage, any presenting distance can be set by the examiner.

For example, the configuration in which a change can be made from a presenting distance at the early stage to a plurality of presenting distances may be a configuration in which a change can be made from a presenting distance at the early stage to one presenting distance. For example, in a case of the configuration in which a change can be made from a presenting distance at the early stage to one presenting distance, a configuration may be adopted in which a change is made between two presenting distances. For example, the two presenting distances may be a presenting distance for far-sight examination (for example, 5 m or the like) and a presenting distance for near-sight examination (for example, 40 cm, 30 cm, or the like). Naturally, a configuration may be adopted in which different presenting distances are set. That is, for example, the presenting distance changing instruction changes a presenting distance between a presenting distance for far-sight examination (far-sight presenting distance) and a presenting distance for near-sight examination (near-sight presenting distance). For example, the anterior ocular segment acquisition device acquires an anterior ocular segment image based on at least any one of the far-sight presenting distance and the near-sight presenting distance. For example, the analysis instruction can perform analysis processing on the acquired anterior ocular segment image to acquire both-eye opened state information. Thereby, it is possible to acquire both-eye opened state information of the examinee based on each of the far-sight examination distance and the near-sight presenting distance. That is, the examinee can confirm whether or not fusion can be performed in both eyes, based on each of the far-sight examination distance and the near-sight presenting distance.

For example, the configuration in which a change can be made from a presenting distance at the early stage to a plurality of presenting distances may be a configuration in which a plurality of changeable presenting distances are set in addition to the presenting distance at the early stage. For example, a configuration may be adopted in which the plurality of presenting distances are arbitrarily set by the examiner. In addition, for example, a configuration may also be adopted in which the plurality of presenting distances are set in advance. In this case, for example, a configuration may be adopted in which the plurality of presenting distances are set for each interval at a predetermined distance. In addition, in this case, for example, a configuration may be adopted in which the plurality of presenting distances are set in accordance with a variety of measurement (for example, measurement based on a far-sight examination distance, measurement based on a middle-sight examination distance, measurement based on a near-sight examination distance, and the like). For example, in a case where a plurality of presenting distances are set in advance, a configuration may also be adopted in which a plurality of presenting distances to be measured can be selected from a plurality of preset presenting distances.

For example, in a case where measurement is performed by making a change to a plurality of presenting distances, a configuration may also be adopted in which the examiner operates the operation portion to make a change to the next presenting distance. In addition, for example, a configuration may also be adopted in which a change to the next presenting distance is automatically made by detecting that measurement has been completed.

For example, when a presenting distance is changed, both-eye opened state information may be acquired until the presenting distance is changed. In this case, for example, the anterior ocular segment acquisition device may acquire at least one or more anterior ocular segment images during the change of the presenting distance by the presenting distance changing instruction. For example, analysis processing may be appropriately performed on the acquired anterior ocular segment image so that the both-eye opened state information is acquired.

For example, the determination instruction may change reference data to perform determination processing in a case where a presenting distance of a visual target is changed by the presenting distance changing instruction. In this case, for example, the determination instruction may change reference data for determining whether both-eye opened state information is favorable or not, in accordance with the presenting distance. For example, since an object at a position close to the subject eye is confirmed in a case of near sight with respect to far sight, a distance between the right and left pupils is decreased. In this state, when reference data for determining whether fusion is favorable or not in a far-sight state is used, it may be determined that the fusion is not favorable in spite of near-sight fusion being performed, because a criterion for determination is different. For example, the optometry apparatus in this embodiment is configured to change reference data for determining whether both-eye opened state information is favorable or not, in accordance with a position where a presenting distance is changed. For example, there is a change in the position of the anterior ocular segment of the subject eye when the examinee performs fusion in accordance with the presenting distance. Thereby, since reference data which is appropriate for determination is set, it is possible to perform the determination with a high level of accuracy.

For example, regarding the change in reference data, a configuration may be adopted in which the amount of correction of the reference data is set. In this case, for example, a configuration may also be adopted in which a presenting distance at the early stage is set in accordance with an examinee, and correction based on a changed distance (the amount of change) of the presenting distance is performed on the reference data of the presenting distance at the early stage. For example, when a presenting distance to be changed is set, the determination instruction may call the amount of correction based on the presenting distance from the memory, and may correct the reference data. Regarding the amount of correction of the reference data, the amount of correction for determining that a both-eye opened state is favorable through simulation, experiment, or the like may be set in advance. For example, a configuration may also be adopted in which the amount of correction of the reference data is arbitrarily set by the examiner. In addition, for example, regarding the amount of correction of the reference data, a configuration may also be adopted in which the amount of correction for determining that a both-eye opened state is favorable in a plurality of presenting distances is set in advance before the measurement of the examinee is started.

For example, regarding the change of the reference data, a configuration may be adopted in which reference data based on a presenting distance is set. For example, regarding the reference data based on a presenting distance, a configuration may also be adopted in which reference data for determining that a both-eye opened state is favorable in a plurality of presenting distances is set in advance before the measurement of the examinee is started. In addition, for example, regarding the reference data based on a presenting distance, reference data for determining that a both-eye opened state is favorable in accordance with a presenting distance through simulation, experiment, or the like may be set in advance.

EXAMPLE

Hereinafter, an optometry apparatus of this example will be described. For example, the optometry apparatus may be a subjective optometry apparatus. For example, the subjective optometry apparatus may include subjective measurement device. In addition, for example, the subjective optometry apparatus may include objective measurement device. In addition, for example, the optometry apparatus may be an objective optometry apparatus. In addition, for example, the objective optometry apparatus may include objective measurement device. In addition, for example, the objective optometry apparatus may include subjective measurement device. In the following description, the subjective optometry apparatus will be described as an example of the optometry apparatus.

Hereinafter, the subjective optometry apparatus of this example will be described. For example, FIG. 1 is a diagram illustrating the exterior of the subjective optometry apparatus 1 according to this example. For example, the subjective optometry apparatus 1 in this example includes a housing 2, a presentation window 3, an operation portion (monitor) 4, a chin mount 5, a base 6, an image capture optical system 100, and the like. For example, the housing 2 accommodates members therein. For example, the housing 2 includes measurement device (a dotted line portion in FIG. 1) 7 therein (details thereof will be described later). For example, the measurement device 7 includes right eye measurement device (right eye measurement means) 7R and left eye measurement device (left eye measurement means) 7L. In this example, the right eye measurement device 7R and the left eye measurement device 7L include the same member. That is, the subjective optometry apparatus 1 includes a pair of right and left subjective measurement device and a pair of right and left objective measurement device. Naturally, the right eye measurement device 7R and the left eye measurement device 7L may be configured such that at least portions of the members thereof are different from each other. In addition, for example, the subjective optometry apparatus 1 may be configured to include only the subjective measurement device.

For example, the presentation window 3 is used to present a visual target to an examinee. For example, visual target luminous flux from the right eye measurement device 7R and the left eye measurement device 7L is projected onto the subject eye E through the presentation window 3.

For example, the monitor (display) 4 is a touch panel. That is, in this example, the monitor 4 functions as an operation portion (controller). The monitor 4 outputs a signal based on an input operation instruction to the controller 70 to be described later. Naturally, the monitor 4 and the operation portion may be configured to be separately provided. For example, the operation portion may be configured to use at least one operation unit such as a mouse, a joystick, or a keyboard.

For example, the monitor 4 may be a display mounted on the main body of the subjective optometry apparatus 1, or may be a display connected to the main body of the subjective optometry apparatus 1. Naturally, the monitor may not be a touch panel type monitor. For example, a display of a personal computer (hereinafter, referred to as a "PC") may be used as the monitor. In addition, for example, a plurality of displays may be used together. For example, a measurement result is displayed on the monitor 4.

For example, the chin mount 5 is used to keep a distance between the subject eye E and the subjective optometry apparatus 1 constant or to suppress considerable movement of a face. For example, the chin mount 5 and the housing 2 are fixed to the base 6. In this example, the chin mount 5 is used to keep a distance between the subject eye E and the subjective optometry apparatus 1 constant, but the invention is not limited thereto. A configuration may also be adopted in which a distance between the subject eye E and the subjective optometry apparatus 1 is kept constant. Examples of a configuration in which a distance between the subject eye E and the subjective optometry apparatus 1 is kept constant include configurations using a forehead protector, a face protector, and the like.

For example, the image capture optical system 100 is constituted by an image capture element and a lens not shown in the drawing. For example, the image capture optical system is used to capture an image of the face of the subject eye.

<Measurement Device>

Figure 2:
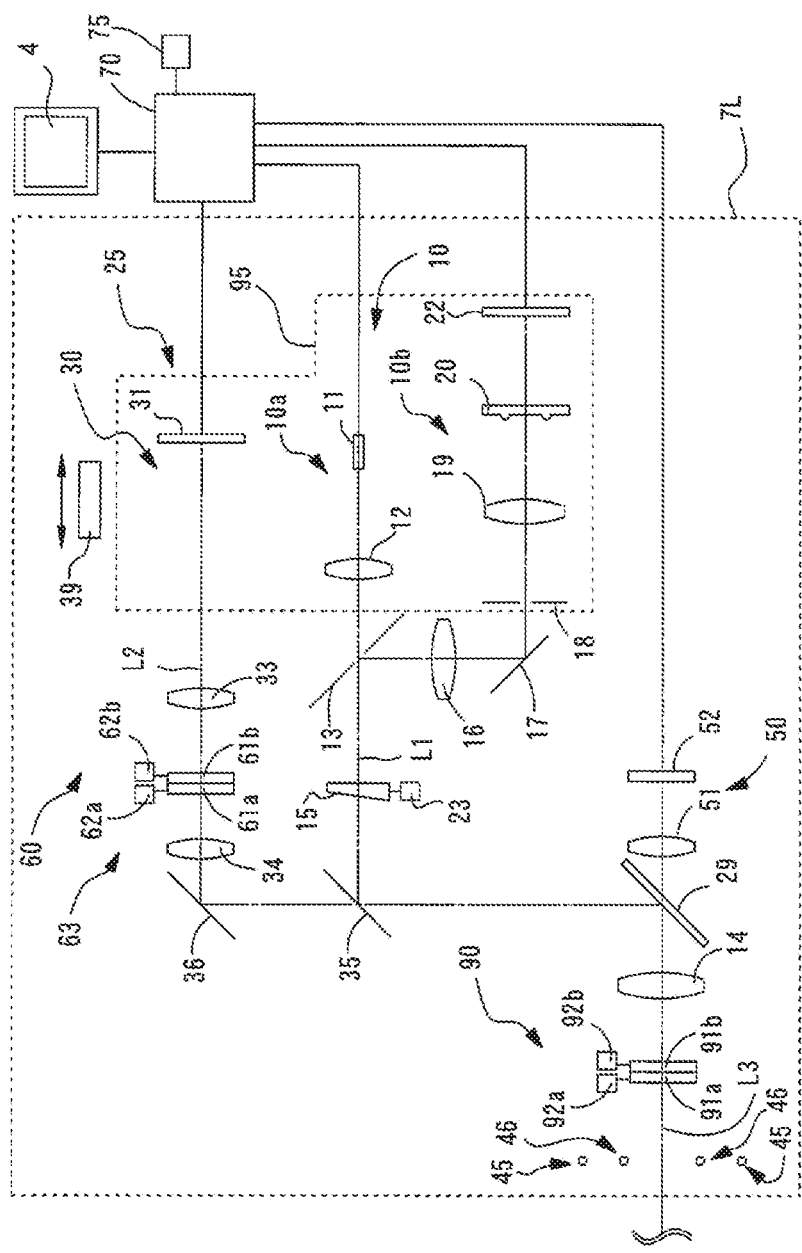
FIG. 2 is a diagram illustrating a configuration of a measurement device.

FIG. 2 is a diagram illustrating a configuration of the measurement device 7. In this example, an example of the left eye measurement device 7L is described. In this example, the right eye measurement device 7R has the same configuration as that of the left eye measurement device 7L, and thus a description thereof will be omitted. For example, the left eye measurement device 7L includes the subjective measurement optical system 25, the objective measurement optical system 10, a first index projection optical system 45, a second index projection optical system 46, and an observation optical system 50.

<Subjective Optical System>

For example, the subjective measurement optical system 25 is used as a portion of a configuration of the subjective measurement device for subjectively measuring an optical characteristic of a subject eye (details thereof will be described later). Examples of the optical characteristic of the subject eye include an eye refractive power, a contrast sensitivity, a binocular vision function (for example, the amount of oblique position, a stereoscopic function, and the like), and the like. In this example, an example of the subjective measurement device for measuring an eye refractive power of a subject eye will be described. For example, the subjective measurement optical system 25 includes a light projecting optical system (visual target projection system) 30, a correction optical system 60, and a correction optical system 90.

For example, the light projecting optical system 30 projects a visual target luminous flux toward the subject eye E. For example, the light projecting optical system 30 includes a display 31, a projection lens 33, a projection lens 34, a reflecting mirror 36, a dichroic mirror 35, a dichroic mirror 29, and an objective lens 14. For example, a visual target luminous flux projected from the display 31 is projected onto the subject eye E through an optical member in order of the projection lens 33, the projection lens 34, the reflecting mirror 36, the dichroic mirror 35, the dichroic mirror 29, and the objective lens 14.

For example, an examination visual target such as a Landolt ring visual target, a fixation target (used during objective measurement to be described later, and the like) to be fixedly viewed by the subject eye E, and the like are displayed on the display 31. For example, a visual target luminous flux from the display 31 is projected toward the subject eye E. In this example, the following description will be given using an example of a case where an LCD is used as the display 31.

For example, the correction optical system 60 includes an astigmatism correction optical system 63 and a driving mechanism 39.

For example, the astigmatism correction optical system 63 is disposed between the projection lens 34 and the projection lens 33. For example, the astigmatism correction optical system 63 is used to correct a cylindrical power, a cylindrical axis, and the like of a subject eye. For example, the astigmatism correction optical system 63 is constituted by two positive cylindrical lenses 61a and 61b having the same focal distance. The cylindrical lenses 61a and 61b are independently rotated about an optical axis L2 by the driving of respective rotation mechanisms 62a and 62b. In this example, the astigmatism correction optical system 63 has been described using an example of a configuration in which the two positive cylindrical lenses 61a and 61b are used, but the invention is not limited thereto. The astigmatism correction optical system 63 may be configured to correct a cylindrical power, a cylindrical axis, and the like. For example, a configuration may also be adopted in which a correction lens is inserted into and removed from an optical path of the light projecting optical system 30.

For example, the display 31 is integrally moved in a direction of the optical axis L2 by the driving mechanism 39 constituted by a motor and a slide mechanism. For example, a presentation position (presenting distance) of a visual target with respect to the examinee's eye is optically changed by the movement of the display 31 during subjective measurement, and thus a spherical refractive power of the subject eye is corrected. That is, a correction optical system of a spherical power is configured by the movement of the display 31. In addition, for example, fogging is applied to the subject eye E by the movement of the display 31 during objective measurement. The correction optical system of the spherical power is not limited thereto. For example, the correction optical system of the spherical power includes a large number of optical elements, and may be configured to perform correction by the optical elements being disposed in the optical path. In addition, for example, a configuration may also be adopted in which a lens disposed in the optical path is moved in the optical axis direction.

In this example, an example of the correction optical system for calibrating a spherical power, a cylindrical power, and a cylindrical axis has been described, but the invention is not limited thereto. For example, a correction optical system for calibrating a prism value may be provided. The correction optical system for the prism value is provided, and thus it is possible to perform correction such that a visual target luminous flux is projected onto a subject eye even when the examinee has heterophoria.

In this example, a description has been given of an example of a configuration in which the astigmatism correction optical system 63 of the cylindrical power and the cylindrical axis and the correction optical system (for example, driver 39) of the spherical power are separately provided, but the invention is not limited thereto. For example, the correction optical system may be configured such that a spherical power, a cylindrical power, and a cylindrical axis are corrected. For example, the correction optical system may be an optical system that modulates a wavefront. In addition, for example, the correction optical system may be an optical system that corrects a spherical power, a cylindrical power, a cylindrical axis, and the like. In this case, for example, the correction optical system may be configured to include a lens disc on which a large number of optical elements (a spherical lens, a cylindrical lens, a dispersing prism, and the like) are disposed on the same circumference. The rotation of the lens disc is controlled by a driving section (actuator or the like), and thus the examiner's desired optical element is disposed on the optical axis L2.

In addition, the rotation of the optical element (for example, a cylindrical lens, a cross cylinder lens, a rotary prism, or the like) which is disposed on the optical axis L2 is controlled by the driving section, and thus the optical element is disposed on the optical axis L2 with the examiner's desired rotation angle. The switching of the optical element disposed on the optical axis L2, and the like may be performed by the operation of an input unit (operation portion) such as the monitor 4.

The lens disc is constituted by one lens disc or a plurality of lens discs. In a case where the plurality of lens discs are disposed, driving sections corresponding to the respective lens discs are provided. For example, as a lens disc group, each lens disc includes an opening (or a lens of 0 D) and a plurality of optical elements. Representative types of lens discs include a spherical lens disc including a plurality of spherical lenses having different powers, a cylindrical lens disc including a plurality of cylindrical lenses having different powers, and an auxiliary lens disc including a plurality of types of auxiliary lenses. At least one of a red filter/green filter, a prism, a cross cylinder lens, a polarizing plate, a Maddox lens, an auto-cross cylinder lens is disposed at the auxiliary lens disc. In addition, the cylindrical lens may be rotatably disposed about the optical axis L2 by the driving section, and the rotary prism and cross cylinder lens may be rotatably disposed about each optical axis by the driving section.

For example, the correction optical system 90 is disposed between the objective lens 14 and a deflection mirror 81 to be described later. For example, the correction optical system 90 is used to correct optical aberration occurring due to the subjective measurement device. For example, the correction optical system 90 is used to correct astigmatism in the optical aberration. For example, the correction optical system 90 is constituted by two positive cylindrical lenses 91a and 91b having the same focal distance. For example, the correction optical system 90 adjusts a cylindrical power and a cylindrical axis to correct astigmatism. The cylindrical lenses 91a and 91b are independently rotated about an optical axis L3 by the rotation of the respective rotation mechanisms 92a and 92b. In this example, a description has been given of an example of the correction optical system 90 configured to use the two positive cylindrical lenses 91a and 91b, but the invention is not limited thereto. The correction optical system 90 may be configured to be capable of calibrating astigmatism. For example, a configuration may also be adopted in which a correction lens is inserted into and removed from the optical axis L3. In this example, a description has been given of an example of a configuration in which the correction optical system 90 is separately disposed, but the invention is not limited thereto. A configuration may also be adopted in which the correction optical system 60 also serves as the correction optical system 90. In this case, the cylindrical power and the cylindrical axis of the subject eye are corrected in accordance with the amount of astigmatism. That is, the correction optical system 60 is driven so as to correct the (corrected) cylindrical power and cylindrical axis which take the amount of astigmatism into consideration. In this manner, for example, complicated control and separate correction optical system for optical aberration are not required by the correction optical system 60 also serving as the correction optical system 90, and thus it is possible to correct optical aberration with a simple configuration.

<Objective Optical System>

For example, the objective measurement optical system 10 is used as a portion of a configuration of the objective measurement device for objectively measuring an optical characteristic of a subject eye (details thereof will be described later). Examples of the optical characteristic of the subject eye include an eye refractive power, an ocular axial length, a cornea shape, and the like. In this example, an example of the objective measurement device for measuring an eye refractive power of a subject eye will be described.

For example, the objective measurement optical system 10 includes a projection optical system 10a, a light receiving optical system 10b, and a correction optical system 90. For example, the projection optical system (light projecting optical system) 10a projects a spot-shaped measurement index onto the fundus of the subject eye E through the pupil central portion of the subject eye E. For example, the light receiving optical system 10b extracts fundus reflected light reflected from the fundus in a ring shape through the pupil peripheral portion, and causes a two-dimensional image capture element to capture a ring-shaped fundus reflected image.

For example, the projection optical system 10a includes a measurement light source 11, a relay lens 12, a hole mirror 13, a prism 15, a driving section (motor) 23, a dichroic mirror 35, a dichroic mirror 29, and an objective lens 14 which are disposed on an optical axis L1 of the objective measurement optical system 10. For example, the prism 15 is a luminous flux deflection member. For example, the driving section 23 is a rotation unit for rotating the prism 15 about the optical axis L1. For example, the light source 11 is conjugated with the subject eye fundus, and a hole portion of the hole mirror 13 is conjugated with the pupil. For example, the prism 15 is disposed at a position away from the position conjugated with the pupil of the subject eye E, and a luminous flux to pass through the prism is eccentric with the optical axis L1. A configuration may also be adopted in which a parallel plane plate is obliquely disposed on the optical axis L1 as a luminous flux deflection member instead of the prism 15.

For example, the dichroic mirror 35 is common to the optical path of the subjective measurement optical system 25 and the optical path of the objective measurement optical system 10. That is, for example, the dichroic mirror 35 has the optical axis L2 of the subjective measurement optical system 25 and the optical axis L1 of the objective measurement optical system 10 as the same axis. For example, a beam splitter 29 which is an optical path branching member reflects a luminous flux of the subjective measurement optical system 25 and measurement light of the projection optical system 10a, and guides the reflected luminous flux and measurement light to the subject eye.

For example, the light receiving optical system 10b shares the objective lens 14, the dichroic mirror 29, the dichroic mirror 35, the prism 15, and the hole mirror 13 with the projection optical system 10a, and includes a relay lens 16 and a mirror 17 which are disposed in an optical path in the reflection direction of the hole mirror 13, and a light receiving diaphragm 18, a collimator lens 19, a ring lens 20, and a two-dimensional image capture element 22 (hereinafter, referred to as an image capture element 22) such as a CCD, which are disposed in an optical path in the reflection direction of the mirror 17. For example, the light receiving diaphragm 18 and the image capture element 22 are conjugated with the subject eye fundus. For example, the ring lens 20 is constituted by a lens portion formed in a ring shape and a light shielding portion obtained by performing coating for light shielding on a region other than the lens portion, and has an optically conjugate positional relationship with the pupil of the subject eye. For example, an output from the image capture element 22 is input to a computational controller 70 (hereinafter, a controller 70).

For example, the dichroic mirror 29 reflects reflected light of the measurement light from the projection optical system 10a based on the subject eye fundus toward the light receiving optical system 10. In addition, for example, the dichroic mirror 29 transmits front eye portion observation light and alignment light, and guides the transmitted light to the observation optical system 50. In addition, for example, the dichroic mirror 35 reflects reflected light of the measurement light from the projection optical system 10a based on the subject eye fundus toward the light receiving optical system 10.

The objective measurement optical system 10 is not limited to the above-described objective measurement optical system, and it is possible to use a well-known objective measurement optical system configured to project a ring-shaped measurement index onto the fundus from the pupil peripheral portion, to extract fundus reflected light from the pupil central portion, and to cause the two-dimensional image capture element to receive light of the ring-shaped fundus reflected image.

The objective measurement optical system 10 is not limited to the above-described objective measurement optical system, and may be a measurement optical system including a light projecting optical system that projects measurement light toward an examinee's fundus and a light receiving optical system in which reflected light acquired by the reflection of the measurement light from the fundus is received by a light receiving element. For example, an eye refractive power measurement optical system may be configured to include a Shack Hartman sensor. Naturally, an apparatus using another measurement method may be used (for example, an apparatus of a phase difference system which projects a slit).

For example, the light source 11 of the projection optical system 10a, the light receiving diaphragm 18, the collimator lens 19, the ring lens 20, and the image capture element 22 of the light receiving optical system 10b are configured to be integrally moved in the optical axis direction. In this example, for example, the light source 11, the light receiving diaphragm 18 of the light receiving optical system 10b, the collimator lens 19, the ring lens 20, and the image capture element 22 of the projection optical system 10a are integrally moved in the direction of the optical axis L1 by the driving mechanism 39 that drives the display 31. That is, the display 31, the light source 11, the light receiving diaphragm 18 of the light receiving optical system 10b, the collimator lens 19, the ring lens 20, and the image capture element 22 of the projection optical system 10a are integrally moved as a driving unit 95 in synchronization with each other. Naturally, a configuration in which these components are separately driven may also be adopted.

For example, the driving unit 95 moves a portion of the objective measurement optical system 10 in the optical axis direction so that an external ring luminous flux is incident on the image capture element 22 with respect to each longitudinal direction. That is, a portion of the objective measurement optical system 10 is moved in the direction of the optical axis L1 in accordance with a spherical refractive error (spherical refractive power) of the subject eye, so that the spherical refractive error is corrected and the light source 11, the light receiving diaphragm 18, and the image capture element 22 are optically conjugated with the subject eye fundus. The position of the driving mechanism 39 to be moved is detected by a potentiometer not shown in the drawing. The hole mirror 13 and the ring lens 20 are disposed so as to be conjugated with the pupil of the subject eye with a fixed magnification, regardless of the amount of movement of the movable unit 25.

In the above-described configuration, measurement light emitted from the light source 11 forms a spot-shaped point light source image on the fundus of the subject eye through the relay lens 12, the hole mirror 13, the prism 15, the dichroic mirror 35, the beam splitter 29, and the objective lens 14. At this time, a pupil projection image (projected luminous flux on the pupil) of the hole portion of the hole mirror 13 is eccentrically rotated at high speed by the prism 15 rotating around the optical axis. The point light source image projected onto the fundus is reflected and scattered, is emitted to the subject eye, is collected by the objective lens 14, and is collected again at the position of the light receiving diaphragm 18 through the beam splitter 29, the dichroic mirror 35, the prism 15 rotated at high speed, the hole mirror 13, the relay lens 16, and the mirror 17, thereby forming a ring-shaped image on the image capture element 22 by the collimator lens 19 and the ring lens 20.

For example, the prism 15 is disposed at an optical path which is common to the projection optical system 10a and the light receiving optical system 10b. For this reason, a reflected luminous flux from the fundus passes through the prism 15 which is the same as that of the projection optical system 10a, and thus backward scanning is performed as if there is no eccentricity of a projected luminous flux and reflected luminous flux (received luminous flux) on the pupil in the subsequent optical systems.

For example, the correction optical system 90 also serves as the subjective measurement optical system 25. Naturally, a configuration may also be adopted in which a correction optical system used in the objective measurement optical system 10 is separately provided.

<First Index Projection Optical System and Second Index Projection Optical System>

In this example, the first index projection optical system 45 and the second index projection optical system 46 are disposed between the correction optical system 90 and the deflection mirror 81. Naturally, the arrangement position of the first index projection optical system 45 and the second index projection optical system 46 are not limited thereto.

In the first index projection optical system 45, a plurality of infrared light sources are disposed on the concentric circle about the optical axis L3 at intervals of 45 degrees, and are disposed so as to be bilaterally symmetrical to each other with a vertical plane passing through the optical axis L3 therebetween. The first index projection optical system 45 emits near infrared light for projecting an alignment index onto the subject eye's cornea. The second index projection optical system 46 is disposed at a position different from the position of the first index projection optical system 45, and includes six infrared light sources. In this case, the first index projection optical system 45 is configured to project an index at an infinite distance onto the cornea of the examinee's eye E from the right-left direction, and the second index projection optical system 46 is configured to project an index at a finite distance onto the cornea of the examinee's eye E from the up-down direction or an oblique direction. In FIG. 2, only portions of the first index projection optical system 45 and the second index projection optical system 46 are illustrated for convenience of description. The second index projection optical system 46 is also used as an anterior ocular segment illumination that illuminates the subject eye's anterior ocular segment. In addition, the second index projection optical system can also be used as an index for measuring the shape of a cornea. In addition, the first index projection optical system 45 and the second index projection optical system 46 are not limited to a dot-shaped light source. For example, the systems may be a ring-shaped light source or a linear light source.

<Observation Optical System>

The observation optical system (image capture optical system) 50 shares the objective lens 14 and the dichroic mirror 29 in the subjective measurement optical system 25 and the objective measurement optical system 10, and includes an imaging lens 51 and a two-dimensional image capture element 52. For example, the image capture element 52 has an imaging surface disposed at a position substantially conjugated with the subject eye's anterior ocular segment. For example, an output from the image capture element 52 is input to the controller 70. Thereby, an anterior ocular segment image of the subject eye is captured by the two-dimensional image capture element 52 and is displayed on the monitor 4. The observation optical system 50 also serves as an optical system that detects an alignment index image formed on the subject eye's cornea by the first index projection optical system 45 and the second index projection optical system 46, and the position of the alignment index image is detected by the controller 70.

<Internal Configuration of Subjective Optometry Apparatus>

Figure 3:
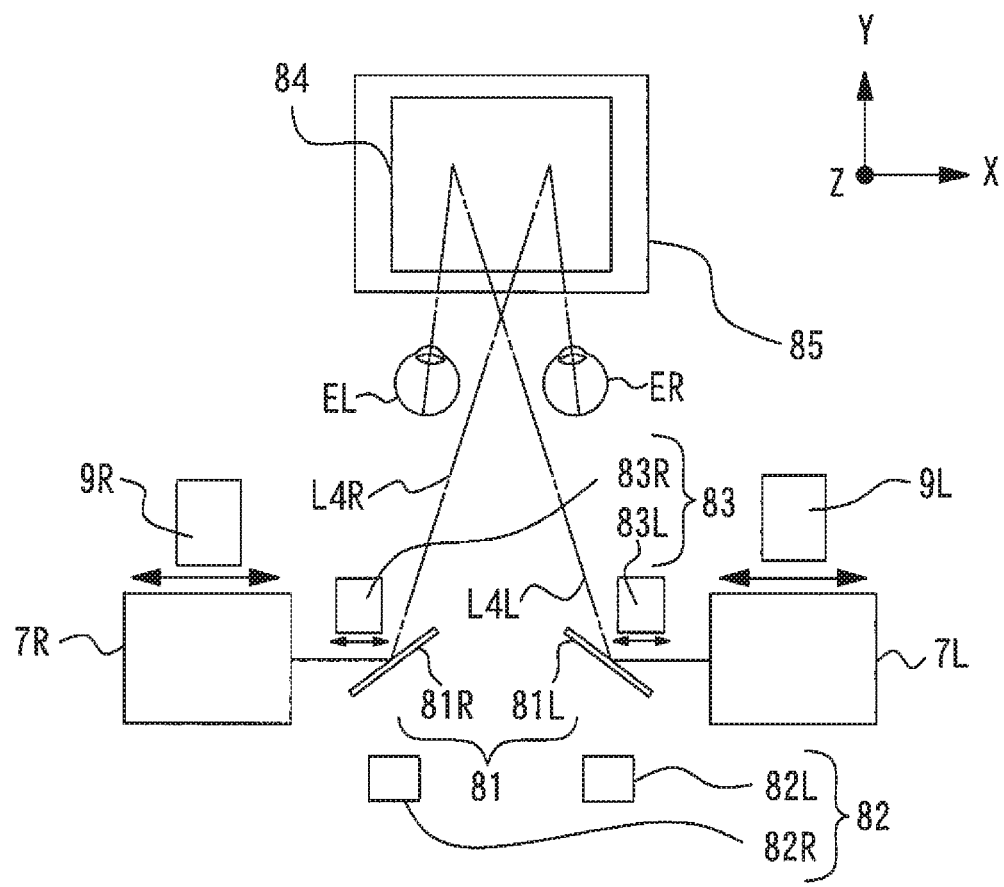
FIG. 3 is a diagram illustrating a schematic configuration when the inside of the subjective optometry apparatus is seen from the front.
Figure 4:
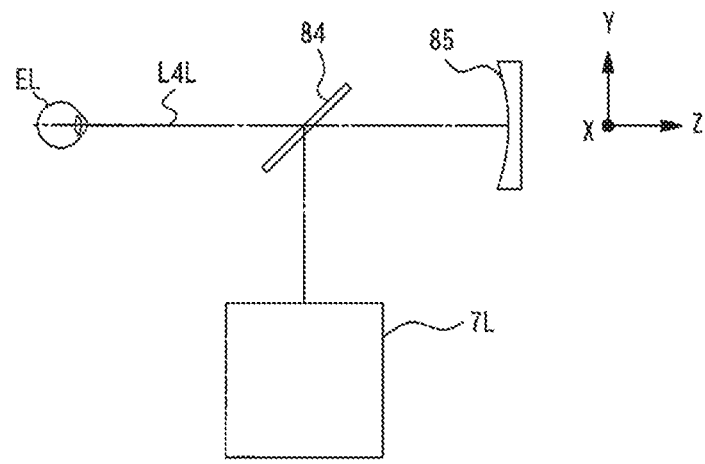
FIG. 4 is a diagram illustrating a schematic configuration when the inside of the subjective optometry apparatus is seen from the side.
Figure 5:
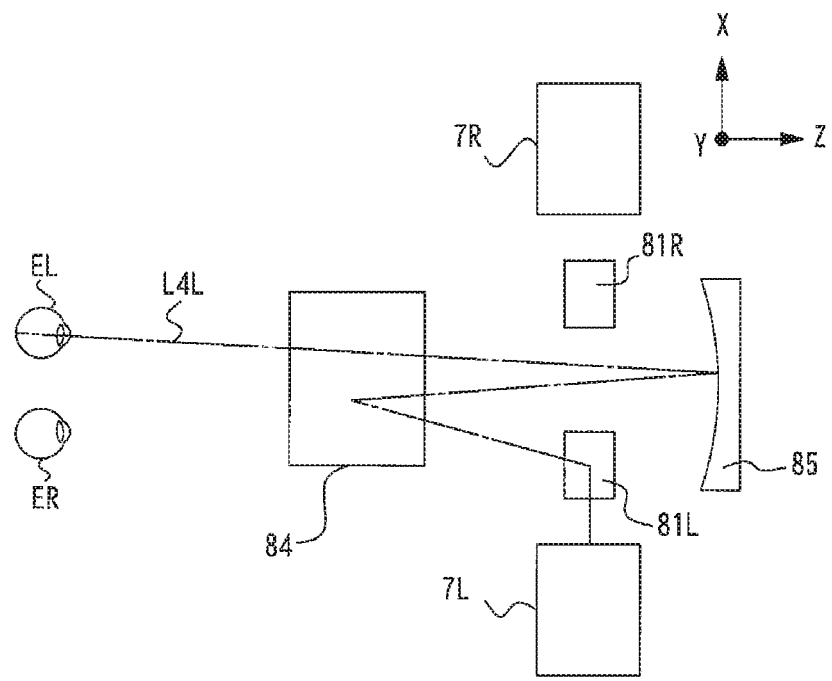
FIG. 5 is a diagram illustrating a schematic configuration when the inside of the subjective optometry apparatus is seen from above.

Hereinafter, the internal configuration of the subjective optometry apparatus 1 will be described. FIG. 3 is a schematic configuration diagram when the inside of the subjective optometry apparatus 1 according to this example is seen from the front (a direction A of FIG. 1). FIG. 4 is a schematic configuration diagram when the inside of the subjective optometry apparatus 1 according to this example is seen from the side (a direction B of FIG. 1). FIG. 5 is a schematic configuration diagram when the inside of the subjective optometry apparatus 1 according to this example is seen from the above (a direction C of FIG. 1). In FIG. 3, an optical axis indicating reflection by a half mirror 84 is omitted for convenience of description. In FIG. 4, only the optical axis of the left eye measurement device 7L is illustrated for convenience of description. In FIG. 5, only the optical axis of the left eye measurement device 7L is illustrated for convenience of description.

For example, the subjective optometry apparatus 1 includes subjective measurement device and objective measurement device. For example, the subjective measurement device includes measurement device 7, a deflection mirror 81, driver 83, driver 82, a half mirror 84, and a concave surface mirror 85. Naturally, the subjective measurement device is not limited to such a configuration. For example, the objective measurement device includes measurement device 7, a deflection mirror 81, a half mirror 84, and a concave surface mirror 85. Naturally, the objective measurement device is not limited to such a configuration.

The subjective optometry apparatus 1 includes right eye driver 9R and left eye driver 9L, and can move the right eye measurement device 7R and the left eye measurement device 7L in the X-direction, respectively. For example, the right eye measurement device 7R and the left eye measurement device 7L are moved, and thus a distance between the deflection mirror 81 and the measurement device 7 is changed, and the presentation position of a visual target luminous flux in the Z-direction is changed. Thereby, it is possible to guide the visual target luminous flux corrected by the correction optical system 60 to the subject eye and to perform adjustment in the Z-direction so that an image of the visual target luminous flux corrected by the correction optical system 60 is formed on the subject eye's fundus.

For example, the deflection mirror 81 includes a right eye deflection mirror 81R and a left eye deflection mirror 81L which are provided as a pair on right and left sides, respectively. For example, the deflection mirror 81 is disposed between the correction optical system 60 and the subject eye. That is, the correction optical system 60 includes a right eye correction optical system and a left eye correction optical system which are provided as a pair on right and left sides respectively. The right eye deflection mirror 81R is disposed between the right eye correction optical system and a right eye ER, and the left eye deflection mirror 81L is disposed between the left eye correction optical system and a left eye ER. For example, it is preferable that the deflection mirror 81 is disposed at a position conjugated with the pupil.

For example, the right eye deflection mirror 81R reflects a luminous flux projected from the right eye measurement device 7R, and guides the luminous flux to the right eye ER. In addition, for example, the right eye deflection mirror reflects the reflected light reflected by the right eye ER, and guides the reflected light to the right eye measurement device 7R. For example, the left eye deflection mirror 81L reflects a luminous flux projected from the left eye measurement device 7L, and guides the luminous flux to the left eye EL. In addition, for example, the left eye deflection mirror reflects the reflected light reflected by the left eye EL, and guides the reflected light to the left eye measurement device 7L. In this example, a description has been given of an example of a configuration in which the deflection mirror 81 is used as a deflection member that reflects a luminous flux projected from the measurement device 7 and guides the luminous flux to the subject eye E, but the invention is not limited thereto. Any deflection member that reflects a luminous flux projected from the measurement device 7 and guides the luminous flux to the subject eye E may be used. Examples of the deflection member include a prism, a lens, and the like.

For example, the driver 83 is constituted by a motor (driving section), and the like. For example, the driver 83 includes driver 83R for driving the right eye deflection mirror 81R, and driver 83L for driving the left eye deflection mirror 81L. For example, the deflection mirror 81 can be moved in the X-direction by the driving of the driver 83. For example, a distance between the right eye deflection mirror 81R and the left eye deflection mirror 81L is changed by the movement of the right eye deflection mirror 81R and the left eye deflection mirror 81L, and thus it is possible to change a distance between a right eye optical path and a left eye optical path in the X-direction in accordance with a distance between the subject eye and the pupil.

For example, the driver 82 is constituted by a motor (driving section) or the like. For example, the driver 82 includes driver 82R for driving the right eye deflection mirror 81R and driver 82L for driving the left eye deflection mirror 81L. For example, the deflection mirror 81 is rotated by the driving of the driver 82. For example, the driver 82 rotates the deflection mirror 81 about a rotation axis in the horizontal direction (X-direction) and a rotation axis in the vertical direction (Y-direction). That is, the driver 82 rotates the deflection mirror 81 in the XY directions. The rotation of the deflection mirror 81 may be performed in either the horizontal direction or the vertical direction. A configuration may also be adopted in which a plurality of deflection mirrors are provided in each of the right eye optical path and the left eye optical path. Examples of the configuration include a configuration in which two deflection mirrors are provided in each of the right eye optical path and the left eye optical path (for example, two deflection mirrors in the right eye optical path, or the like). In this case, one deflection mirror may be rotated in the X-direction, and the other deflection mirror may be rotated in the Y-direction. For example, the deflection mirror 81 is rotated, and thus it is possible to optically correct the position of an image to be formed by deflecting an apparent luminous flux for the image of the correction optical system 60 to be formed in front of the subject eye.

For example, the concave surface mirror 85 is shared by the right eye measurement device 7R and the left eye measurement device 7L. For example, the concave surface mirror 85 is shared by a right eye optical path including a right eye correction optical system and a left eye optical path including a left eye correction optical system. That is, the concave surface mirror 85 is disposed at a position where the concave surface mirror passes through both the right eye optical path including the right eye correction optical system and the left eye optical path including the left eye correction optical system. Naturally, the concave surface mirror 85 may be configured not to be shared. A configuration may also be adopted in which the concave surface mirror is provided in each of the right eye optical path including the right eye correction optical system and the left eye optical path including the left eye correction optical system. For example, the concave surface mirror 85 guides a visual target luminous flux having passed through the correction optical system to the subject eye, and forms an image of the visual target luminous flux having passed through the correction optical system in front of the subject eye. In this example, a configuration in which the concave surface mirror 85 is used has been described as an example, but the invention is not limited thereto. It is possible to use various optical members. Examples of the optical member to be used may include a lens, a planar mirror, and the like.

For example, the concave surface mirror 85 also serves as subjective measurement device and objective measurement device. For example, a visual target luminous flux projected from the subjective measurement optical system 25 is projected onto the subject eye through the concave surface mirror 85. In addition, for example, measurement light projected from the objective measurement optical system 10 is projected onto the subject eye through the concave surface mirror 85. In addition, for example, reflected light of the measurement light projected from the objective measurement optical system 10 is guided to the light receiving optical system 10b of the objective measurement optical system 10 through the concave surface mirror 85. In this example, a configuration in which the reflected light of the measurement light from the objective measurement optical system 10 is guided to the light receiving optical system 10b of the objective measurement optical system 10 through the concave surface mirror 85 has been described as an example, but the invention is not limited thereto. A configuration may also be adopted in which the reflected light of the measurement light from the objective measurement optical system 10 does not go through the concave surface mirror 85.

In more detail, for example, in this example, an optical axis between the concave surface mirror 85 and the subject eye E in the subjective measurement device and an optical axis between the concave surface mirror 85 and the subject eye E in the objective measurement device are configured as substantially the same axis. In this example, the optical axis L2 of the subjective measurement optical system 25 and the optical axis L1 of the objective measurement optical system 10 are combined with each other by the dichroic mirror 35, and are thus configured as the same axis.

Hereinafter, the optical path of the subjective measurement device will be described. For example, the subjective measurement device reflects a visual target luminous flux having passed through the correction optical system 60 in a direction of the subject eye by the concave surface mirror 85 to thereby guide the visual target luminous flux to the subject eye, and forms an image of the visual target luminous flux having passed through the correction optical system 60 in front of the subject eye so as to optically have a predetermined examination distance. That is, the concave surface mirror 85 reflects the visual target luminous flux so as to convert the visual target luminous flux into a substantially parallel luminous flux. For this reason, a visual target image seen from the examinee looks as if the visual target image is located farther than the actual distance between the subject eye E and the display 31. That is, the concave surface mirror 85 is used, and thus it is possible to present the visual target image to the examinee so that the image of the visual target luminous flux is seen at the predetermined examination distance.

A more detailed description will be given. In the following description, the left eye optical path will be described as an example. The right eye optical path also has the same configuration as that of the left eye optical path. For example, in the subjective measurement device for the left eye, a visual target luminous flux projected from the display 31 of the left eye measurement device 7L is incident on the astigmatism correction optical system 63 through the projection lens 33. The visual target luminous flux having passed through the astigmatism correction optical system 63 is incident on the correction optical system 90 through the reflecting mirror 36, the dichroic mirror 35, the dichroic mirror 29, and the objective lens 14. The visual target luminous flux having passed through the correction optical system 90 is projected toward the left eye deflection mirror 81L from the left eye measurement device 7L. The visual target luminous flux emitted from the left eye measurement device 7L and reflected by the left eye deflection mirror 81 is reflected toward the concave surface mirror 85 by the half mirror 84. The visual target luminous flux reflected by the concave surface mirror reaches the left eye EL through the half mirror 84.

Thereby, a visual target image corrected by the correction optical system 60 based on a spectacle wearing position of the left eye EL (for example, a position separated from the vertex of the cornea at approximately 12 mm) is formed on the fundus of the left eye EL. Therefore, this is equivalent to the arrangement of the astigmatism correction optical system 63 in front of the eye and the adjustment of a spherical power by a correction optical system (in this example, driving of the driving mechanism 39) of a spherical power, and thus the examinee can collimate the visual target image in a natural state through the concave surface mirror 85. In this example, the right eye optical path also has the same configuration as that of the left eye optical path, and the visual target image corrected by a pair of right and left correction optical systems 60 is formed on the fundi of both subject eyes, based on spectacle wearing positions (for example, positions apart from the vertexes of the corneas at approximately 12 mm) of both the subject eyes ER and EL. In this manner, the examinee responds to the examiner while looking straight at the visual target in a state of a natural sight, attempts correction by the correction optical system 60 until an examination visual target is seen properly, and subjectively measures an optical characteristic of the subject eye based on the correction value thereof.

Subsequently, the optical path of the objective measurement device will be described. In the following description, the left eye optical path will be described as an example. The right eye optical path also has the same configuration as that of the left eye optical path. For example, in the objective measurement device for the left eye, measurement light emitted from the light source 11 of the projection optical system 10a in the objective measurement optical system 10 is incident on the correction optical system 90 through the relay lens 12 to the objective lens 14. The measurement light having passed through the correction optical system 90 is projected toward the left eye deflection mirror 81L from the left eye measurement device 7L. The measurement light emitted from the left eye measurement device 7L and reflected by the left eye deflection mirror 81 is reflected toward the concave surface mirror 85 by the half mirror 84. The measurement light reflected by the concave surface mirror reaches the left eye EL through the half mirror 84, thereby forming a spot-shaped point light source image on the fundus of the left eye EL. At this time, a pupil projection image (a projected luminous flux on the pupil) of the hole portion of the hole mirror 13 is eccentrically rotated at high speed by the prism 15 rotating about the optical axis.

Light of the point light source image formed on the fundus of the left eye EL is reflected and scattered, and is emitted to the subject eye E, is collected by the objective lens 14 through the optical path through which the measurement light is transmitted, and passes through the dichroic mirror 29, the dichroic mirror 35, the prism 15, the hole mirror 13, the relay lens 16, and the mirror 17. The reflected light having passed through these components from the dichroic mirror to the mirror 17 is collected again on the opening of the light receiving diaphragm 18, is converted into a substantially parallel luminous flux (a case of a normal vision eye) by the collimator lens 19, is extracted as a ring-shaped luminous flux by the ring lens 20, and is received by the image capture element 22 as a ring image. The received ring image is analyzed, and thus it is possible to objectively measure an optical characteristic of the subject eye.

<Controller>

For example, the controller 70 includes a CPU (processor), a RAM, a ROM, and the like. For example, the CPU of the controller 70 controls each member of the subjective optometry apparatus 1. For example, the RAM temporarily stores various pieces of information. Various programs for controlling the operation of the subjective optometry apparatus 1, visual target data for various examinations, an initial value, and the like are stored in the ROM of the controller 70. The controller 70 may be constituted by a plurality of controllers (that is, a plurality of processors).

For example, a non-volatile memory (storage section) 72, a monitor (also serves as an operation portion in this example) 4, various members, and the like are electrically connected to the controller 70. The non-volatile memory (hereinafter, referred to as a memory) 72 is a non-fugitive storage medium capable of holding stored contents even when the supply of power is stopped. For example, a hard disc drive, a flash ROM, an OCT device 1, a USB memory capable of being detachably mounted to the subjective optometry apparatus 1, or the like can be used as the non-volatile memory 72. For example, a control program for controlling the subjective measurement device and the objective measurement device is stored in the memory 72.

<Control Operation>

Hereinafter, a control operation of the subjective optometry apparatus 1 will be described. FIG. 6 is a flow chart illustrating a flow of a control operation in this example. The examiner puts the examinee's chin on the chin mount 5 to instruct the examinee to observe the presentation window 3. The examiner instructs the examinee to fixedly view a fixation target displayed on the display 31, and then performs alignment on the subject eye.

<Alignment Operation (S1)>

When an alignment start switch is selected by the examiner, the controller 70 starts automatic alignment (S1). In this example, a case where an optical characteristic of the subject eye during far measurement will be described as an example. Similarly to the far measurement, it is also possible to measure an optical characteristic of the subject eye during near measurement.

For example, the controller 70 detects the position of the pupil of each of the right and left subject eyes from a face image captured by the image capture optical system 100. For example, when the position of the pupil is detected, the controller 70 controls the subjective optometry apparatus 1 so that an anterior ocular segment image is displayed on the monitor 4. For example, the controller 70 respectively drives the right eye deflection mirror 81R and the left eye deflection mirror 81L, and rotates the mirrors in the XY directions. In addition, for example, when the position of the pupil is detected, the controller 70 can move the right eye measurement device 7R and the left eye measurement device 7L in the X-direction, respectively. That is, the controller 70 drives the deflection mirror 81 to perform alignment in the XY directions, and drives the measurement device 7 to perform alignment in the Z-direction.

In this example, a description has been given of an example of a configuration in which alignment in the XYZ directions is adjusted by the driving of the deflection mirror 81 and the measurement device 7, but the invention is not limited thereto. Any configuration may also be adopted as long as a positional relationship between the subject eye, the subjective measurement device, and the objective measurement device can be adjusted. That is, any configuration may also be adopted as long as the XYZ directions can be adjusted so that an image corrected by the correction optical system 60 is formed on the fundus of the subject eye. For example, a configuration may also be adopted in which the subjective optometry apparatus 1 is moved by providing a configuration in which the subjective optometry apparatus 1 can be moved in the XYZ directions with respect to the chin mount 5. In addition, for example, as a configuration in which the deflection mirror 81 and a measurement unit can be integrally moved in the XYZ directions, a configuration in which adjustment in the XYZ directions can be performed may be adopted. In addition, for example, a configuration may also be adopted in which adjustment in the XYZ directions can be performed by only the deflection mirror 81. In this case, examples of the configuration include a configuration in which the deflection mirror 81 is moved in the Z-direction so that the deflection mirror 81 is rotated and a distance between the deflection mirror 81 and the measurement unit is changed. For example, in the alignment control, both subject eyes may be displayed on the monitor 4, and the alignment control of both subject eyes may be performed on the same screen. In addition, for example, in the alignment control, after one subject eye is displayed on the monitor 4 and after the alignment control of one subject eye is completed, the other subject eye may be displayed on the monitor 4, and the alignment control of the other subject eye may be performed. In addition, for example, a configuration may also be adopted in which the alignment control of the other subject eye may be performed based on an alignment control result of one subject eye.

For example, the controller 70 detects a positional shift of the image of the correction optical system 60 with respect to the subject eye. For example, the controller 70 controls the driver based on the detected detection result, and optically corrects the position of the image formed by deflecting an apparent luminous flux for guiding the image of the correction optical system 60 to the subject eye. In this manner, the subjective optometry apparatus 1 in this example has a configuration in which a positional shift between the subject eye and the correction optical system is detected and the position of the image formed is optically corrected. Thereby, the positional shift between the subject eye and the correction optical system is corrected, and thus it is possible to use the apparatus at an appropriate position and to perform measurement with a high level of accuracy.

<Objective Measurement (S2)>

The controller 70 emits an objective measurement start trigger signal (hereinafter, referred to as a trigger signal) for starting objective measurement (objective measurement) (S2) based on the output of an alignment completion signal. When the trigger signal for starting the objective measurement is emitted, the controller 70 emits a measurement luminous flux from the objective measurement optical system 10. In this case, each measurement luminous flux is reflected by the concave surface mirror 85 through the deflection mirrors 81R and 81L, and is then projected onto the fundus of the subject eye. After measurement light reflected from the fundus is reflected by the deflection mirror 81R (81L) through the concave surface mirror 85, a measurement image is captured by the image capture element 22.

For example, in the measurement of an objective eye refractive power, preliminary measurement of an eye refractive power is first performed, and the display 31 is moved in a direction of the optical axis L2 based on a result of the preliminary measurement, and thus fogging may be applied to the subject eye E. That is, the display 31 may be moved once to a position where the subject eye E is brought into focus. Thereafter, the measurement of the eye refractive power may be performed on the subject eye to which the fogging is applied. In this measurement, a measurement image is captured by the image capture element 22, and an output signal from the image capture element 22 is stored as image data (measurement image) in the memory 72. Thereafter, the controller 70 analyzes a ring image stored in the memory 72 to obtain the value of a refractive power in each longitudinal direction. The controller 70 performs predetermined processing on the refractive power to obtain objective eye refractive powers (objective values) of S (spherical power), C (astigmatic power), and A (astigmatic axis angle) of the examinee's eye during far measurement. The obtained objective values during far measurement are stored in the memory 72.

In the above-described measurement of the objective eye refractive power, the controller 70 may control the correction optical system 90 and may correct optical aberration occurring in the optical path of the objective measurement optical system 10. In this case, the amount of correction based on a refraction power measured by the objective measurement optical system 10 is acquired from the memory 72, and the correction optical system 90 is controlled based on the acquired amount of aberration correction.

More specifically, the amount of correction is set in accordance with the eye refractive power obtained through the preliminary measurement, and the correction optical system 90 is driven based on the set amount of correction. Thereby, this measurement is performed in a state where aberration occurring in the optical path of the objective measurement optical system 10 is corrected, and thus it is possible to measure the objective eye refractive power with a high level of accuracy. In a case where an eye refractive power is consecutively measured (for example, this measurement is performed a plurality of times), the correction optical system 90 may be controlled based on measurement results.

In the above description, the objective eye refractive power has been measured through far measurement. However, the invention is not limited thereto, an objective eye refractive power through near measurement which is an eye refractive power in a state where a visual target is presented at a near measurement distance may be measured. The measurement of the objective eye refractive power may be executed for the right and left eyes at the same time, and may be individually performed for each of the right and left eyes.

<Subjective Measurement (S3)>

Subsequently, subjective measurement (S3) is performed. When the measurement of the objective refractive power is completed and the monitor (in this example, also serves as an operation portion) 4 is operated, switching to a subjective far sight measurement (subjective refractive power measurement) mode is performed.

For example, the controller 70 may control the display 31 to display a required visual acuity value visual target on the optical axis L2 (for example, a visual target having a visual acuity value of 0.8). When an initial presentation visual target is presented to the subject eye, the examiner performs far sight measurement of the examinee. When a predetermined switch of the monitor 4 is pressed, a visual acuity value visual target to be presented is switched.

For example, the examiner performs switching to a visual target having a visual acuity value higher by one step in a case where the examinee's answer is a correct answer. On the other hand, the examiner performs switching to a visual target having a visual acuity value lower by one step in a case where the examinee's answer is a wrong answer. That is, the controller 70 may switch a visual target based on a signal for changing a visual acuity value which is received from the monitor 4.

In addition, the examiner may change a correction power of the correction optical system 60 by using the monitor 4 to obtain a far measurement subjective value (a spherical power S, an astigmatic power C, and an astigmatic axis angle A) of the subject eye. The correction power of the correction optical system 60 may be set to be a correction power for each of the right and left eyes, or may be set to be the same correction power for the right and left eyes.

Hereinafter, a description will be given of a case where subjective measurement is performed in a both-eye opened state. For example, when an operation portion 4 is operated in a subjective far-sight measurement mode by the examiner and an one-eye examination mode not shown in the drawing is selected, the controller 70 controls the right eye measurement device 7R and the left eye measurement device 7L. For example, in one-eye examination mode, the examiner operates the operation portion 4 to select a subject eye on a side to be first measured out of the right and left subject eyes. For example, when the subject eye to be measured is selected, the controller 70 starts the control of the light projecting optical system 30 in each of the right eye measurement device 7R and the left eye measurement device 7L. For example, the display 31 in each of the right eye measurement device 7R and the left eye measurement device 7L is controlled and a visual target is projected onto each of the right and left subject eyes so that one-eye examination is started. As the one-eye examination, measurement may be started from any subject eye out of the right and left subject eyes. In this example, a description will be given of an example of a case where measurement is performed from the right subject eye.

For example, the controller 70 emits a visual target luminous flux from the light projecting optical system 30 for the right eye, and projects a first visual target including an examination visual target and a first background visual target onto the right subject eye. In addition, for example, the controller 70 emits a visual target luminous flux from the light projecting optical system 30 for the left eye, and projects a second visual target including a second background visual target having the same pattern as that of the first background visual target onto the left subject eye.

For example, the controller 70 may display a predetermined visual acuity value visual target in a case where the first visual target and the second visual target are displayed. Naturally, at least one of the first visual target and the second visual target may be displayed by the predetermined visual acuity value visual target. For example, the predetermined visual acuity value visual target may be set based on a measurement result measured through objective measurement. In addition, for example, regarding the predetermined visual acuity value visual target, any visual acuity value visual target may be set by the examiner. In addition, for example, regarding the predetermined visual acuity value visual target, a preset visual acuity value visual target may be set.

Figure 7A:
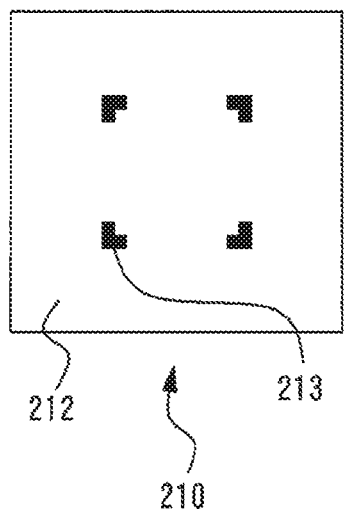
FIGS. 7A and 7B are diagrams illustrating a visual target presented to right and left subject eyes during the measurement of the right subject eye.
Figure 7B:
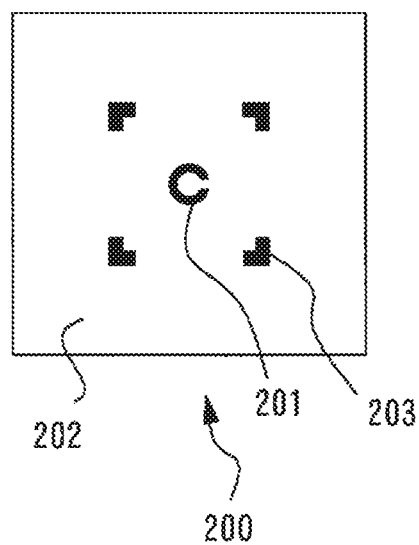

FIG. 7 is a diagram illustrating a visual target presented to the right and left subject eyes during the measurement of the right subject eye. FIG. 7(a) illustrates a visual target projected onto the left subject eye. FIG. 7(b) illustrates a visual target projected onto the right subject eye. For example, in this example, an examination visual target is projected onto the eye on which measurement is to be performed. For example, the first visual target 200 is projected onto the right subject eye. For example, the second visual target 210 is projected onto the left subject eye.

For example, in this example, as the first visual target 200, the examination visual target 201, the first background visual target 202, and the first fusion visual target 203 are displayed. For example, the examination visual target 201 is switched based on the examinee's response so that subjective measurement regarding the right subject eye is performed. For example, in this example, as the second visual target 210, the second background visual target 212 and the second fusion visual target 213 are displayed.

For example, in this example, the examination visual target 201 is a Landolt ring visual target. Naturally, the examination visual target 201 is not limited to the Landolt ring visual target, and may be a different examination visual target.

For example, as the first background visual target 202 and the second background visual target 212, a white background visual target is used. Naturally, the first background visual target 202 and the second background visual target 212 are not limited to the white background visual target, and may be a different background visual target. For example, the first background visual target 202 and the second background visual target 212 are background visual targets having the same pattern.

For example, the first fusion visual target 203 and the second fusion visual target 213 are black frame-shaped visual targets. For example, the first fusion visual target 203 is displayed so as to surround the examination visual target 201. For example, the first fusion visual target 203 and the second fusion visual target 213 are fusion visual targets having the same pattern. For example, the first fusion visual target 203 and the second fusion visual target 213 are used to supplement the examinee's fusion. In this example, a configuration in which black frame-shaped visual targets are used as the first fusion visual target 203 and the second fusion visual target 213 is described as an example, but the invention is not limited thereto. For example, visual targets having various patterns may be used as the first fusion visual target and the second fusion visual target. For example, as the visual targets having various patterns, various visual targets may be used in at least any one of a shape, a size, a color, a shape, a luminance value, and a contrast. In this example, a configuration in which the first fusion visual target 203 and the second fusion visual target 213 are displayed has been adopted, but a configuration may be adopted in which the first fusion visual target 203 and the second fusion visual target 213 are not displayed.

For example, a state where the examination visual target 201, the first background visual target 202, and the first fusion visual target 203 are presented to the right subject eye is set. That is, for example, a state where the first background visual target 202 having the examination visual target 201 presented thereto is presented to the right subject eye is set. For example, a state where the second background visual target 212 and the second fusion visual target 213 are presented to the left subject eye is set. That is, for example, a state where the second background visual target 212 having the examination visual target not presented thereto is presented to the left subject eye is set. Thereby, a state where the examination visual target 201 can be observed in the right subject eye to be measured is set, and a state where the examination visual target is not seen in the left subject eye not to be measured is set. That is, it is possible to perform the measurement of the right subject eye in an opened state without performing shielding on the left subject eye not to be measured. That is, it is possible to perform the measurement of the right subject eye (one-eye measurement) in a both-eye opened state.

For example, the examiner switches the examination visual target 201 by operating the operation portion 4 to perform subjective measurement regarding the right subject eye based on the examinee's response, and the examiner operates the operation portion 4 to start the measurement of the left subject eye when the measurement of the right subject eye is completed. Naturally, a configuration may also be adopted in which it is detected that the measurement of one subject eye has been completed, and the measurement of the other subject eye is automatically started.

For example, in the measurement of the left subject eye, the controller 70 emits a visual target luminous flux from the light projecting optical system 30 for the right eye, and projects a third visual target (for example, equivalent to the first visual target 200 during the measurement of the right subject eye) including an examination visual target and a third background visual target onto the left subject eye. For example, the controller 70 emits a visual target luminous flux from the light projecting optical system 30 for the right eye, and projects a fourth visual target (for example, equivalent to the second visual target 210 during the measurement of the right subject eye) including a fourth background visual target having the same pattern as that of the third background visual target onto the right subject eye.

Figure 8A:
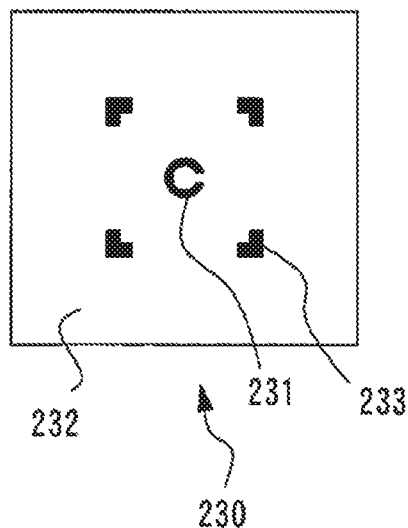
FIGS. 8A and 8B are diagrams illustrating a visual target presented to right and left subject eyes during the measurement of the left subject eye.
Figure 8B:
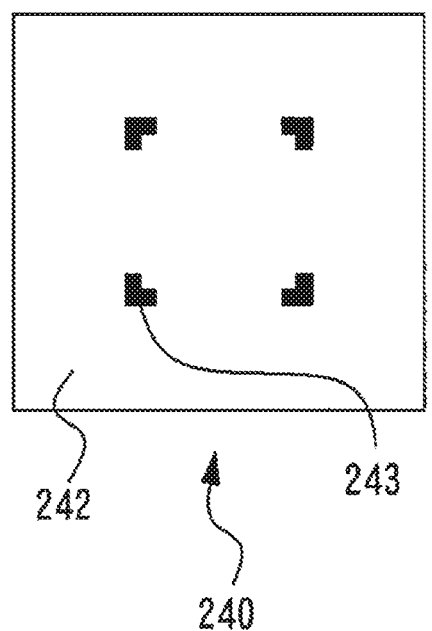
Figure 9:
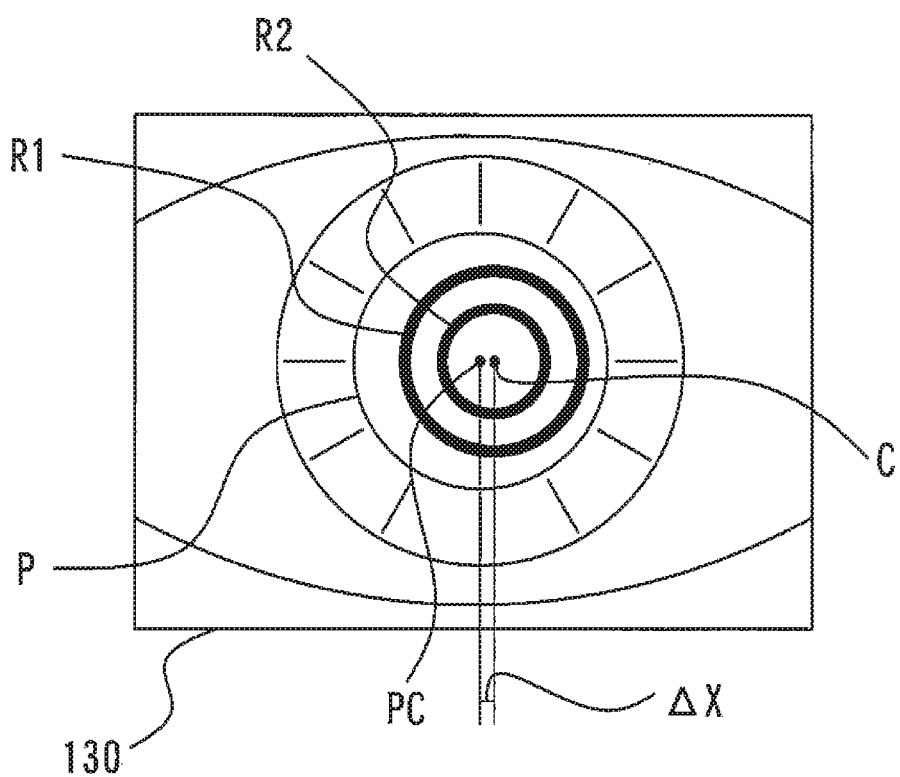
FIG. 9 is a diagram illustrating an anterior ocular segment image of the right subject eye.

FIG. 8 is a diagram illustrating a visual target presented to the right and left subject eyes during the measurement of the left subject eye. FIG. 8(a) illustrates a visual target projected onto the left subject eye. FIG. 8(b) illustrates a visual target projected onto the right subject eye. For example, the fourth visual target 240 is projected onto the right subject eye. For example, the third visual target 230 is projected onto the left subject eye.

For example, in this example, as the third visual target 230, the examination visual target 231, the third background visual target 232, and the third fusion visual target 233 are displayed. For example, the examination visual target 231 is switched based on the examinee's response so that subjective measurement regarding the left subject eye is performed. For example, in this example, as the fourth visual target 240, the fourth background visual target 242 and the fourth fusion visual target 243 are displayed. The third visual target 230 and the fourth visual target 240 have the same configurations as those of the first visual target 200 and the second visual target 210, and thus a description thereof will not be repeated. In this manner, it is possible to perform the measurement of the left subject eye in an opened state without performing shielding on the right subject eye not to be measured. That is, it is possible to perform the measurement of the left subject eye (one-eye measurement) in a both-eye opened state.

As described above, for example, the subjective optometry apparatus in this example projects a visual target including an examination visual target and a background visual target onto one subject eye out of the right and left subject eyes, and projects a visual target including a background visual target having the same pattern as that of the background visual target, which is projected onto one subject eye, onto the other subject eye out of the right and left subject eyes. With such a configuration, a member, complicated control, and the like for reproducing a both-eye opened state when performing one-eye examination in the both-eye opened state are not required. For this reason, it is possible to easily perform subjective measurement under a natural state and to perform measurement with a high level of accuracy.

In addition, for example, the subjective optometry apparatus in this example projects a fusion visual target onto one subject eye out of the right and left subject eyes, and projects a fusion visual target having the same pattern as that of the fusion visual target, which is projected onto one subject eye, onto the other subject eye. Thereby, even when examination is performed in a both-eye opened state, it is possible to facilitate fusion in both eyes and to perform measurement with a high level of accuracy. In particular, this is useful for a case where the visual target projected onto the subject eye does not include an examination visual target. For example, the subject eye on a side where the examination visual target is displayed is set to be in a state where fusion is facilitated with the examination visual target as a target. However, in a case where an examination visual target is not displayed on one eye, there is no examination visual target serving as a target, and thus fusion is not likely to be performed. For example, even when the visual target projected onto the subject eye does not include an examination visual target, a fusion visual target is presented to a background visual target, and thus it is possible to facilitate fusion with the fusion visual target as a target and to facilitate fusion in both eyes.

In addition, for example, the fusion visual target is configured to have a frame shape so as to surround the examination visual target, and thus the fusion visual target is set to be larger than the examination visual target, which makes a fusion operation with respect to the examination visual target more effective. Thereby, it is possible to acquire a measurement result with higher accuracy.

As described above, after subjective value is obtained through far measurement, switching to a subjective near sight measurement mode may be performed. When a near measurement mode is set, the controller 70 may control the light projecting optical system 30, may change a convergence angle by the deflection mirror 81, and may present a visual target at a near measurement position. A visual target presenting distance in a near measurement examination may be arbitrarily changed based on an operation signal received from the operation portion 4. As a result, the visual target presenting distance is changed from a far measurement position to a near measurement position. In the near measurement examination, a presenting distance of a visual target may be changed at a near measurement position to subjectively obtain an addition and an adjusting power.

In this case, for example, the controller 70 may acquire the amount of aberration correction based on the visual target presenting distance from the memory 72, and may control the correction optical system 90 based on the acquired amount of aberration correction. In addition, in a case where the visual target presenting distance is changed, the controller 70 may change the amount of aberration correction by the correction optical system 90 in accordance with the changed visual target presenting distance. Thereby, even when the visual target presenting distance is changed, the visual target with reduced aberration is presented. In this case, the controller 70 may change the amount of aberration correction in accordance with a correction power to which the visual target presenting distance is added.

Further, the controller 70 may control a light deflection member in accordance with the change in the presentation position of the visual target, and may change convergence angles of right and left visual target luminous fluxes. In this case, for example, the controller 70 may acquire the amount of aberration correction based on a deflection angle of the light deflection member corresponding to the convergence angle from the memory 72, and may control the correction optical system 90 based on the acquired amount of aberration correction. In addition, in a case where the convergence angle of the visual target luminous flux is changed, the controller 70 may change the amount of aberration correction of the correction optical system 90 in accordance with the changed convergence angle. Thereby, even when the convergence angle is changed, a visual target with reduced aberration is presented.

Similarly to the far measurement examination, in a near measurement examination, for example, the examiner may change a correction power of the correction optical system 60 by using a predetermined switch of the operation portion 4, and may measure a subjective eye refractive power (near measurement subjective value) in a state where a near measurement visual target is presented. In the near measurement examination, the controller 70 may change the amount of aberration correction of the correction optical system 90 in accordance with the change in correction power.

<Determination of Fusion State (S5)>

For example, in this example, in subjective measurement in a both-eye opened state, a configuration is adopted in which it is determined whether or not both-eye fusion based on the right and left subject eyes is favorably performed during the measurement. In this example, it is determined whether or not both-eye fusion is favorably performed during the subjective measurement (S5). Naturally, a configuration may also be adopted in which it is determined whether or not both-eye fusion is favorably performed during the objective measurement. In this example, measurement in a subjective far-sight measurement mode will be described as an example.

For example, in this example, a description will be given of an example of a case where it is determined whether or not both-eye fusion during the measurement of the right subject eye is favorably performed in the subjective measurement (S3). Naturally, it is possible to use the technique of this disclosure even during the measurement of the left subject eye or during the measurement of both eyes. For example, the technique related to the determination of a fusion state is not necessarily applied to only subjective measurement. For example, the technique related to the determination of a fusion state may also be applied in the objective measurement (S2).

For example, in the subjective measurement, the controller 70 emits a visual target luminous flux from the light projecting optical system 30 for the right eye, and projects a first visual target including an examination visual target and a first background visual target onto the right subject eye. In addition, for example, the controller 70 emits a visual target luminous flux from the light projecting optical system 30 for the left eye, and projects a second visual target including a second background visual target having the same pattern as that of the first background visual target onto the left subject eye. For example, in this example, the first visual target 200 is projected onto the right subject eye. For example, the second visual target 210 is projected onto the left subject eye. For example, the examination visual target 201 is switched based on the examinee's response so that subjective measurement regarding the right subject eye is performed.

Here, for example, the controller 70 acquires anterior ocular segment images of the respective right and left subject eyes during the measurement of an optical characteristic of the right subject eye. For example, the controller 70 turns on the light sources of the first index projection optical system 45 and the second index projection optical system 46 which are respectively provided in the right eye measurement device 7R and the left eye measurement device 7L. When a predetermined trigger signal is generated, the controller 70 captures the anterior ocular segment images of the respective right and left subject eyes.

In this example, an anterior ocular segment image of the left eye and an anterior ocular segment image of the right eye are acquired. FIG. 8 is a diagram illustrating an anterior ocular segment image of the right subject eye. For example, in an acquired anterior ocular segment image 130, a ring index R1 based on the light source of the first index projection optical system 45 is displayed, and a ring index R2 based on the second index projection optical system 46 is displayed on the inner side of the ring index R1. In addition, a pupil P is displayed in the anterior ocular segment image 130.

For example, the controller 70 performs analysis processing on the acquired anterior ocular segment image 130 to acquire both-eye opened state information. For example, in this example, the controller 70 detects the pupil P and an index image (for example, the ring index R2) through analysis processing, and acquires a pupil center position (pupil center position information) PC and a cornea apex position (cornea apex position information) C. For example, the pupil center position PC can be acquired by detecting the position of the pupil P and obtaining the center position thereof. For example, the cornea apex position C can be acquired by detecting the index image (ring image R2) and obtaining the center position thereof. Naturally, the cornea apex position C may be obtained from the ring image R1, or may be obtained from both the ring image R1 and the ring image R2.

For example, the controller 70 obtains an edge position of the pupil P from the anterior ocular segment image 130. For example, the controller 70 detects the edge position of the pupil P by detecting a rise and a fall in a luminance value, and acquires contour information on the pupil P. Thereby, the controller 70 can detect the position of the pupil P. For example, the controller 70 detects the pupil center position PC based on the contour information on the pupil P.

For example, the controller 70 obtains an edge position of the index image from the anterior ocular segment image 130. For example, the controller 70 detects the edge position of the index image by detecting a rise and a fall in a luminance value, and acquires contour information on the index image. Thereby, the controller 70 can detect the position of the index image. For example, the controller 70 detects the center position of the index image based on the contour information on the index image. For example, the controller 70 can detect the cornea apex position C by detecting the center position of the index image.

For example, the controller 70 acquires the both-eye opened state information by calculating the amount of shift ΔX between the pupil center position PC and the cornea apex position C. That is, in a case where the position of the subject eye is shifted, a gaze direction changes, and thus the amount of shift between the pupil center position PC and the cornea apex position C is increased. In this example, a case where the amount of shift between the pupil center position PC and the cornea apex position C is calculated as the both-eye opened state information is described as an example, but the invention is not limited thereto. For example, the both-eye opened state information may be at least anyone of pupil information, cornea apex information, and the like. For example, the pupil information may be at least any one of distance-between-pupils information, pupil position information, pupil positional shift information, and the like. For example, the cornea apex information may be at least any one of cornea apex position information, distance-between-corneas information, cornea apex shift information, and the like. For example, the both-eye opened state information may be information calculated from the pupil position information and the cornea apex position information.

Next, for example, the controller 70 acquires determination information by determining whether the acquired both-eye opened state information is favorable or not. In this example, for example, the controller 70 acquires the determination information by determining whether or not the amount of shift ΔX exceeds reference data. For example, a preset threshold value may be used as the reference data. For example, the controller 70 determines that the both-eye opened state is not favorable in a case where the amount of shift ΔX exceeds a threshold value. On the other hand, for example, the controller 70 determines that the both-eye opened state is favorable in a case where the amount of shift ΔX is equal to or less than the threshold value.

For example, the controller 70 performs determination processing to acquire determination information indicating whether or not a determination result is favorable. For example, the controller 70 acquires both-eye opened states of the respective right and left subject eyes and performs determination processing thereon. Thereby, the controller 70 can acquire determination information on the right and left subject eyes. For example, the controller 70 may acquire respective pieces of determination information as the determination information on the right and left subject eyes. In addition, for example, the controller 70 may acquire comprehensive determination information based on the comprehensive determination information on the right and left subject eyes, as the determination information on the right and left subject eyes. In this example, a case where the comprehensive determination information is acquired will be described as an example.

For example, the controller 70 acquires respective pieces of determination information on the right and left subject eyes. Subsequently, the controller 70 acquires the comprehensive determination information based on the respective pieces of determination information on the right and left subject eyes. For example, the controller 70 determines that the both-eye opened state information is favorable in a case where both the respective pieces of determination information on the right and left subject eyes are determination information indicating that the determination result is favorable, and acquires determination information based on the determination result. On the other hand, the controller 70 determines that the both-eye opened state information is not favorable in a case where at least one of the respective pieces of determination information on the right and left subject eyes is determination information indicating that the determination result is not favorable, and acquires determination information based on the determination result.

For example, the controller 70 outputs the acquired determination information. For example, in this example, the controller 70 displays the determination information on the monitor 4. Naturally, a configuration may also be adopted in which the controller 70 prints the determination information.

As described above, for example, the optometry apparatus in this embodiment is configured to acquire anterior ocular segment images of the respective right and left subject eyes during the measurement of an optical characteristic of the subject eye in a both-eye opened state, and to acquire both-eye opened state information by performing analysis processing on the acquired anterior ocular segment images. In addition, the optometry apparatus is configured to determine whether being favorable or not based on the acquired both-eye opened state information and to output a determination result. Thereby, it is possible to easily confirm whether or not a fusion state of the subject eye during measurement is favorable or not, and to acquire a measurement result under a state where the fusion state is favorable. Thereby, it is possible to obtain a highly accurate measurement result.

In this example, both-eye opened state information may be acquired when a presenting distance is changed. In this example, for example, in a case where the presenting distance is changed, the controller 70 controls the display 31 of the light projecting optical system 30 to change the presenting distance. In addition, for example, the controller 70 may change the angles of the deflection mirrors 81R and 81L in accordance with the presenting distance to change a convergence angle. For example, the controller 70 may start measurement after changing the presenting distance, and may acquire determination information of a both-eye opened state. For example, the controller 70 may acquire the determination information of the both-eye opened state even while changing the presenting distance.

What is claimed is:

1. An optometry apparatus comprising:
an optical characteristic measurement device configured to measure refractive power of right and left subject eyes in a both-eye opened state by projecting a visual target onto the subject eyes;
an anterior ocular segment acquisition device configured to acquire anterior ocular segment images of the right and left subject eyes by the optical characteristic measurement device during the measurement of the refractive power of the subject eyes in the both-eye opened state; and
a controller configured to execute:
an analysis instruction for performing analysis processing on the anterior ocular segment images acquired by the anterior ocular segment acquisition device to acquire both-eye opened state information for confirming a fusion state of the subject eyes in the both-eye opened state;
a determination instruction for determining whether the both-eye opened state information acquired by the analysis instruction is favorable or not, to acquire determination information; and
an output instruction for outputting the determination information acquired by the determination instruction.

2. The optometry apparatus according to claim 1, wherein the analysis instruction detects pupil positions of each of the right and left subject eyes by performing analysis processing on the anterior ocular segment images, and acquires the both-eye opened state information based on the pupil positions.

3. The optometry apparatus according to claim 1, wherein the controller executes a distance changing instruction for changing a presenting distance of the visual target to the right and left subject eyes by the optical characteristic measurement device,
wherein in a case where the presenting distance is changed according to the distance changing instruction, the anterior ocular segment acquisition instruction causes the optometry apparatus to acquire the anterior ocular segment images during the measurement of the refractive power of the subject eyes in the both-eye opened state in the changed presenting distance, and
wherein the analysis instruction causes the optometry apparatus to perform the analysis processing on the anterior ocular segment images in the changed presenting distance, and acquires the both-eye opened state information in the changed presenting distance.

4. The optometry apparatus according to claim 1, wherein the determination instruction causes the optometry apparatus to change reference data for determining whether the both-eye opened state information is favorable or not, in accordance with a presenting distance of the visual target to the right and left subject eyes.

5. The optometry apparatus according to claim 1, wherein the optical characteristic measurement device includes a subjective measurement device including a correction optical system which is disposed in an optical path of a light projecting optical system projecting a visual target luminous flux toward the subject eye and changes an optical characteristic of the visual target luminous flux, and subjectively measuring the refractive power of the subject eyes.

6. The optometry apparatus according to claim 1, wherein the optical characteristic measurement device includes an objective measurement device configured to objectively measure the refractive power of the subject eyes, the objective measurement device including a measurement optical system configured to emit measurement light to a fundus of the subject eye and receives reflected light thereof.

7. The optometry apparatus according to claim 5, wherein the light projecting optical system includes a right eye light projecting optical system and a left eye light projecting optical system which are respectively provided as a pair on right and left sides, and emits the visual target luminous flux toward the subject eye to project the visual target onto the subject eye,
the correction optical system includes a right eye correction optical system and a left eye correction optical system which are respectively provided as a pair on right and left sides, is disposed in the optical path of the light projecting optical system, and changes the optical characteristic of the visual target luminous flux, the controller controls the optometry apparatus to emit a visual target luminous flux from one of the right eye light projecting optical system and the left eye light projecting optical system, projects a first visual target onto one of the right and left subject eyes, emit a visual target luminous flux from the other of the right eye light projecting optical system and the left eye light projecting optical system, and projects a second visual target onto the other of the right and left subject eyes, the first visual target includes an examination visual target and a first background visual target, and the second visual target includes a second background visual target having the same pattern as that of the first background visual target.

8. The optometry apparatus according to claim 7, wherein the first visual target includes a first fusion visual target, and the second visual target includes a second fusion visual target having the same pattern as that of the first fusion visual target.

9. The optometry apparatus according to claim 8, wherein the controller changes the first fusion visual target and the second fusion visual target in a case where a change signal is received.

10. The optometry apparatus according to claim 9, wherein the controller executes a change signal output instruction for outputting the change signal in a case where the examination visual target is changed.

11. The optometry apparatus according to claim 8, wherein the first fusion visual target is configured to have a frame shape so as to surround the examination visual target.

12. The optometry apparatus according to claim 1, wherein the controller executes the determination instruction by comparing the acquired both eye opened state information and reference data.

13. An optometry apparatus configured to subjectively measure an optical characteristic of a subject eye, the optometry apparatus comprising:
- a light projecting optical system that includes a right eye light projecting optical system and a left eye light projecting optical system which are respectively provided as a pair on right and left sides, and projects a visual target onto the subject eyes by emitting a visual target luminous flux toward the subject eyes;
- a correction optical system that includes a right eye correction optical system and a left eye correction optical system which are respectively provided as a pair on right and left sides, is disposed in an optical path of the light projecting optical system, and changes an optical characteristic of the visual target luminous flux; and
- a controller for controlling the light projection optical system to emit a visual target luminous flux from one 1 of the right eye light projecting optical system and the left eye light projecting optical system, project a first visual target onto one of the right and left subject eyes, emit a visual target luminous flux from the other of the right eye light projecting optical system and the left eye light projecting optical system, and project a second visual target onto the other of the right and left subject eyes, wherein the first visual target includes an examination visual target and a first background visual target, wherein the second visual target includes a second background visual target having the same pattern as that of the first background visual target;

wherein the first visual target includes a first fusion visual target, and the second visual target includes a second fusion visual target having the same pattern as that of the first fusion visual target.

14. A non-transitory computer readable recording medium storing a computer readable program for controlling an optometry apparatus including a refractive power measurement device for measuring a refractive power of right and left subject eyes in a both-eye opened state by projecting a visual target onto the subject eyes, the computer readable program when executed by a processor of the optometry apparatus causing the optometry apparatus to execute:
- an anterior ocular segment acquisition instruction for acquiring anterior ocular segment images of the right and left subject eyes by the refractive power measurement device during the measurement of the refractive power of the subject eyes in the both-eye opened state;
- an analysis instruction for performing analysis processing on the anterior ocular segment images acquired by the anterior ocular segment acquisition step to acquire both-eye opened state information for confirming a fusion state of the subject eyes in the both-eye opened state;
- a determination instruction for determining whether the both-eye opened state information acquired by the analysis step is favorable or not, to acquire determination information; and
- an output instruction for outputting the determination information acquired by the determination step.

* * * * *